(12) United States Patent
Paton et al.

(10) Patent No.: US 7,892,549 B2
(45) Date of Patent: *Feb. 22, 2011

(54) TREATMENT WITH ANTI-ERBB2 ANTIBODIES

(75) Inventors: Virginia E. Paton, Oakland, CA (US); Steven Shak, Burlingame, CA (US); Susan D. Hellmann, San Carlos, CA (US)

(73) Assignee: Genentech, Inc., South San Francisco, CA (US)

( * ) Notice: Subject to any disclaimer, the term of this patent is extended or adjusted under 35 U.S.C. 154(b) by 1827 days.

This patent is subject to a terminal disclaimer.

(21) Appl. No.: 10/356,824

(22) Filed: Feb. 3, 2003

(65) Prior Publication Data

US 2004/0037823 A9 Feb. 26, 2004

Related U.S. Application Data

(63) Continuation of application No. 09/208,649, filed on Dec. 10, 1998.

(60) Provisional application No. 60/069,346, filed on Dec. 12, 1997.

(51) Int. Cl.
  A61K 39/395 (2006.01)
  C07K 16/28 (2006.01)
  C07K 16/30 (2006.01)

(52) U.S. Cl. .............. 424/143.1; 424/130.1; 424/133.1; 424/134.1; 424/135.1; 424/136.1; 424/138.1; 424/141.1; 424/152.1; 424/155.1; 424/156.1; 424/172.1; 424/174.1

(58) Field of Classification Search .............. 424/130.1, 424/133.1, 138.1, 141.1, 143.1, 155.1, 174.1, 424/134.1, 135.1, 136.1, 152.1, 156.1, 172.1
See application file for complete search history.

(56) References Cited

U.S. PATENT DOCUMENTS

| | | |
|---|---|---|
| 4,017,471 A | 4/1977 | Davies |
| 4,753,894 A | 6/1988 | Frankel et al. |
| 4,935,341 A | 6/1990 | Bargmann et al. |
| 4,943,533 A | 7/1990 | Mendelsohn et al. |
| 4,968,603 A | 11/1990 | Slamon et al. |
| 4,975,278 A | 12/1990 | Senter et al. |
| 4,994,558 A | 2/1991 | Armour et al. |
| 5,169,774 A | 12/1992 | Frankel et al. |
| 5,183,884 A | 2/1993 | Kraus et al. |
| 5,288,477 A | 2/1994 | Bacus |
| 5,359,046 A | 10/1994 | Capon et al. |
| 5,367,060 A | 11/1994 | Vandlen et al. |
| 5,401,638 A | 3/1995 | Carney et al. |
| 5,464,751 A | 11/1995 | Greene et al. |
| 5,480,968 A | 1/1996 | Kraus et al. |
| 5,514,554 A | 5/1996 | Bacus |
| 5,571,894 A | 11/1996 | Wels et al. |
| 5,578,482 A | 11/1996 | Lippman et al. |
| 5,587,458 A | 12/1996 | King et al. |
| 5,604,107 A | 2/1997 | Carney et al. |
| 5,641,869 A | 6/1997 | Vandlen et al. |
| 5,663,144 A | 9/1997 | Greene et al. |
| 5,677,171 A | 10/1997 | Hudziak et al. |
| 5,705,157 A | 1/1998 | Greene |
| 5,720,937 A | 2/1998 | Hudziak et al. |
| 5,720,954 A | 2/1998 | Hudziak et al. |
| 5,725,856 A | 3/1998 | Hudziak et al. |
| 5,726,023 A | 3/1998 | Cheever et al. |
| 5,728,687 A | 3/1998 | Bissery |
| 5,747,261 A | 5/1998 | King et al. |
| 5,770,195 A | 6/1998 | Hudziak et al. |
| 5,772,997 A | 6/1998 | Hudziak et al. |
| 5,776,427 A | 7/1998 | Thorpe et al. |
| 5,783,186 A | 7/1998 | Arakawa et al. |
| 5,783,404 A | 7/1998 | Koski |
| 5,801,005 A | 9/1998 | Cheever et al. |
| 5,804,396 A | 9/1998 | Plowman |
| 5,821,337 A | 10/1998 | Carter et al. |
| 5,824,311 A | 10/1998 | Greene et al. |
| 5,834,229 A | 11/1998 | Vandlen et al. |
| 5,837,243 A | 11/1998 | Deo et al. |
| 5,837,523 A | 11/1998 | Greene et al. |
| 5,840,525 A | 11/1998 | Vandlen et al. |
| 5,846,538 A | 12/1998 | Cheever et al. |

(Continued)

FOREIGN PATENT DOCUMENTS

EP 0599274 A1 6/1994

(Continued)

OTHER PUBLICATIONS

Kim, K.-M. et al, Int. J. Cancer, 102: 428-434, 2002.*

(Continued)

*Primary Examiner*—Alana M. Harris
*Assistant Examiner*—Anne L Holleran
(74) *Attorney, Agent, or Firm*—Arnold & Porter LLP; Diane Marschang; Ginger R. Dreger

(57) ABSTRACT

The present invention concerns the treatment of disorders characterized by the overexpression of ErbB2. More specifically, the invention concerns the treatment of human patients susceptible to or diagnosed with cancer overexpressing ErbB2 with a combination of an anti-ErbB2 antibody and a chemotherapeutic agent other than an anthracycline, e.g. doxorubicin or epirubicin.

17 Claims, 1 Drawing Sheet

U.S. PATENT DOCUMENTS

| | | |
|---|---|---|
| 5,846,749 A | 12/1998 | Slamon et al. |
| 5,856,089 A | 1/1999 | Wang et al. |
| 5,856,110 A | 1/1999 | Vandlen et al. |
| 5,859,206 A | 1/1999 | Vandlen et al. |
| 5,869,445 A | 2/1999 | Cheever et al. |
| 5,876,712 A | 3/1999 | Cheever et al. |
| 5,877,305 A | 3/1999 | Huston et al. |
| 5,908,835 A | 6/1999 | Bissery |
| 5,910,486 A | 6/1999 | Curiel et al. |
| 5,922,845 A | 7/1999 | Deo et al. |
| 5,925,519 A | 7/1999 | Jensen et al. |
| 5,939,531 A | 8/1999 | Wels et al. |
| 5,977,322 A | 11/1999 | Marks et al. |
| 5,985,553 A | 11/1999 | King et al. |
| 5,994,071 A | 11/1999 | Ross et al. |
| 6,015,567 A | 1/2000 | Hudziak et al. |
| 6,028,059 A | 2/2000 | Curiel et al. |
| 6,054,297 A | 4/2000 | Carter et al. |
| 6,054,561 A | 4/2000 | Ring |
| 6,123,939 A | 9/2000 | Shawver et al. |
| 6,165,464 A | 12/2000 | Hudziak et al. |
| 6,214,388 B1 | 4/2001 | Benz et al. |
| 6,214,863 B1 | 4/2001 | Bissery |
| 6,267,958 B1 | 7/2001 | Andya et al. |
| 6,270,765 B1 | 8/2001 | Deo et al. |
| 6,316,462 B1 | 11/2001 | Bishop et al. |
| 6,333,348 B1 | 12/2001 | Vogel et al. |
| 6,339,142 B1 | 1/2002 | Basey et al. |
| 6,387,371 B1 | 5/2002 | Hudziak et al. |
| 6,395,272 B1 | 5/2002 | Deo et al. |
| 6,395,712 B1 | 5/2002 | Hung et al. |
| 6,399,063 B1 | 6/2002 | Hudziak et al. |
| 6,407,213 B1 | 6/2002 | Carter et al. |
| 6,458,356 B1 | 10/2002 | Arakawa et al. |
| 6,512,097 B1 | 1/2003 | Marks et al. |
| 6,627,196 B1 | 9/2003 | Baughman et al. |
| 6,639,055 B1 | 10/2003 | Carter et al. |
| 6,685,940 B2 | 2/2004 | Andya et al. |
| 6,719,971 B1 | 4/2004 | Carter et al. |
| 6,800,738 B1 | 10/2004 | Carter et al. |
| 6,821,515 B1 | 11/2004 | Cleland et al. |
| 7,041,292 B1 | 5/2006 | Sliwkowski |
| 7,060,268 B2 | 6/2006 | Andya et al. |
| 7,097,840 B2 | 8/2006 | Erickson et al. |
| 2001/0014326 A1 | 8/2001 | Andya et al. |
| 2002/0001587 A1 | 1/2002 | Erickson et al. |
| 2002/0076408 A1 | 6/2002 | Buchsbaum |
| 2002/0155527 A1 | 10/2002 | Stuart et al. |
| 2003/0103973 A1 | 6/2003 | Rockwell et al. |
| 2003/0108545 A1 | 6/2003 | Rockwell et al. |
| 2003/0147884 A1 | 8/2003 | Paton et al. |
| 2003/0170234 A1 | 9/2003 | Hellmann |
| 2003/0202972 A1 | 10/2003 | Andya et al. |
| 2004/0013660 A1 | 1/2004 | Bissery |
| 2004/0037823 A9 | 2/2004 | Paton et al. |
| 2004/0037824 A1 | 2/2004 | Baughman et al. |
| 2004/0106161 A1 | 6/2004 | Bossenmaier et al. |
| 2004/0236078 A1 | 11/2004 | Carter et al. |
| 2004/0258685 A1 | 12/2004 | Brunetta et al. |
| 2005/0002928 A1 | 1/2005 | Hellmann |
| 2005/0208043 A1 | 9/2005 | Adams et al. |
| 2005/0238640 A1 | 10/2005 | Sliwkowski |
| 2005/0244417 A1 | 11/2005 | Ashkenazi et al. |
| 2006/0013819 A1 | 1/2006 | Kelsey |
| 2006/0018899 A1 | 1/2006 | Kao et al. |
| 2006/0034840 A1 | 2/2006 | Agus |
| 2006/0034842 A1 | 2/2006 | Adams et al. |
| 2006/0073143 A1 | 4/2006 | Adams et al. |
| 2006/0083739 A1 | 4/2006 | Sliwkowski |
| 2006/0088523 A1 | 4/2006 | Andya et al. |
| 2006/0099201 A1 | 5/2006 | Andya et al. |
| 2006/0121044 A1 | 6/2006 | Amler et al. |
| 2006/0165702 A1 | 7/2006 | Allison et al. |
| 2006/0188509 A1 | 8/2006 | Derynck et al. |
| 2006/0193854 A1 | 8/2006 | Adams et al. |
| 2006/0198843 A1 | 9/2006 | Adams et al. |
| 2006/0204505 A1 | 9/2006 | Sliwkowski et al. |
| 2006/0210561 A1 | 9/2006 | Baughman et al. |
| 2006/0228745 A1 | 10/2006 | Mass |
| 2006/0275305 A1 | 12/2006 | Bryant |
| 2006/0275306 A1 | 12/2006 | Andya et al. |
| 2007/0020261 A1 | 1/2007 | Sliwkowski et al. |
| 2007/0026001 A1 | 2/2007 | Ashkenazi et al. |
| 2007/0037228 A1 | 2/2007 | Moecks et al. |
| 2007/0166753 A1 | 7/2007 | Mass |
| 2007/0184055 A1 | 8/2007 | Sliwkowski |
| 2007/0202516 A1 | 8/2007 | Mass |
| 2007/0224203 A1 | 9/2007 | Friess et al. |
| 2007/0269429 A1 | 11/2007 | Kelsey et al. |
| 2007/0292419 A1 | 12/2007 | Hellmann |

FOREIGN PATENT DOCUMENTS

| | | |
|---|---|---|
| EP | 616812 A1 | 9/1994 |
| EP | 0711565 B1 | 8/1998 |
| JP | 3-240498 | 10/1991 |
| JP | 5-117165 | 5/1993 |
| JP | 5-170667 | 7/1993 |
| JP | 5-213775 | 8/1993 |
| JP | 5-317084 | 12/1993 |
| JP | 95006982 B2 | 1/1995 |
| JP | 7-59588 | 3/1995 |
| JP | 2761543 B2 | 6/1998 |
| JP | 2895105 B2 | 5/1999 |
| WO | WO 87/07646 | 12/1987 |
| WO | WO 89/06692 | 7/1989 |
| WO | WO 89/10412 | 11/1989 |
| WO | WO 91/02062 | 2/1991 |
| WO | WO 91/05264 | 4/1991 |
| WO | WO 92/10573 | 6/1992 |
| WO | WO 93/03741 | 3/1993 |
| WO | WO 93/12220 | 6/1993 |
| WO | WO 93/16185 | 8/1993 |
| WO | WO 93/21232 | 10/1993 |
| WO | WO 93/21319 | 10/1993 |
| WO | WO 94/00136 | 1/1994 |
| WO | WO 94/22478 | 10/1994 |
| WO | WO 94/28127 | 12/1994 |
| WO | WO 95/16051 | 6/1995 |
| WO | WO 95/17507 | 6/1995 |
| WO | WO 95/28485 | 10/1995 |
| WO | WO 96/07321 | 3/1996 |
| WO | WO 96/16673 | 6/1996 |
| WO | WO 96/18409 | 6/1996 |
| WO | WO 96/40789 | 12/1996 |
| WO | WO 97/00271 | 1/1997 |
| WO | WO 97/20858 | 6/1997 |
| WO | WO 97/27848 | 8/1997 |
| WO | WO 97/38731 | 10/1997 |
| WO | WO 98/02463 | 1/1998 |
| WO | WO 98/17797 | 4/1998 |
| WO | WO 98/18489 | 5/1998 |
| WO | WO 98/33914 | 8/1998 |
| WO | WO 98/45479 | 10/1998 |
| WO | WO 99/24401 | 5/1999 |
| WO | WO 99/25320 | 5/1999 |
| WO | WO 99/31140 | 6/1999 |
| WO | WO 00/61145 | 10/2000 |
| WO | WO 00/61185 | 10/2000 |
| WO | WO 00/69460 A1 | 11/2000 |
| WO | WO 01/87334 | 11/2001 |
| WO | WO 02/055106 | 7/2002 |

WO    WO 2007/145862 A2    12/2007

OTHER PUBLICATIONS

Nabholtz, J.M., et al, Breast Cancer Research and Treatment, 64(1): p. 82, #327, 2000.*
Nabholtz, J. M., et al., European Journal of Cancer, 37(suppl. 6): S190, #695, 2001.*
Perez et al., Seminars in Oncology, 23(5, suppl 11): 41-45, Oct. 1996.*
van Oosterom et al., "Docetaxel (Taxotere), a review of preclinical and clinical experience. Part II: Clinical experience" Anti-Cancer Drugs (Abstract only) 6(3):356-368 (Jun. 1995).
Albanell et al., "Trastuzumab, a humanized anti-HER2 monoclonal antibody, for the treatment of breast cancer" Drugs of Today 35(12):931-946 (1999).
"Aminoglutethimide" Martindale—The Complete Drug Reference—Monographs (website version of product information) pp. 1-4 (2003).
Argiris and DiGiovanna, "Synergistic interactions between tamoxifen and HERCEPTIN TM" Proceedings of the American Association for Cancer Research (Abstract #4565) 41:718 (Mar. 2000).
"Arimidex (anastrozole) Tablets" Physicians' Desk Reference (website version of product information) pp. 1-14 (2003).
"Aromasin (exemestane tablets)" Physicians' Desk Reference (website version of product information) pp. 1-9 (2003).
Benz et al., "Estrogen-dependent, tamoxifen-resistant tumorigenic growth of MCF-7 cells transfected with HER2/neu" Breast Cancer Research & Treatment 24(2):85-95 (1992).
Brueggemeier, R., "Aromatase, aromatase inhibitors, and breast cancer" American Journal of Therapeutics 8(5):333-344 (Sep.-Oct. 2001).
"A concerted attack on cancer" Scrip Magazine 2617(Review Issue 2000):68-70 (Feb. 14, 2001).
Dati et al., "Inhibition of c-erbB-2 oncogene expression by estrogens in human breast cancer cells" Oncogene 5(7):1001-1006 (Jul. 1990).
"Femara (letrozole tablets)" Physicians' Desk Reference (website version of product information) pp. 1-13 (2003).
Grem et al., "A phase II evaluation of combination chemotherapy plus aminoglutethimide in women with metastatic or recurrent breast carcinoma. An Eastern Cooperative Oncology Group Pilot Study" American Journal of Clinical Oncology 11(5):528-534 (Oct. 1988).
Hamilton and Piccart, "The contribution of molecular markers to the prediction of response in the treatment of breast cancer: a review of the literature on HER-2, p53 and BCL-2" Annals of Oncology 11(6):647-663 (Jun. 2000).
Kaufmann et al., "Exemestane is superior to megestrol acetate after tamoxifen failure in postmenopausal women with advanced breast cancer: Results of a phase III randomized double-blind trial" Journal of Clinical Oncology 18(7):1399-1411 (Apr. 2000).
Konecny et al., "New drugs in breast cancer therapy: Current position and future perspectives" Gynaekologisch-Geburtshilfliche Rundschau (English language abstract only) 37(2):54-61 (Oct. 1997).
Kunisue et al., "Anti-HER2 antibody enhances the growth inhibitory effect of anti-oestrogen on breast cancer cells expressing both oestrogen receptors and HER2" British Journal of Cancer 82(1):46-51 (Jan. 2000).
Lohrisch and Piccart, "Breast cancer: new aspects of adjuvant hormonal therapy" Annals of Oncology 11(Suppl. 3):13-25 (2000).
Mizukami et al., "Effects of tamoxifen, medroxyprogesterone acetate and estradiol on tumor growth and oncogene expression in MCF-7 breast cancer cell line transplanted into nude mice" Anticancer Research 11(3):1333-1338 (May-Jun. 1991).
Pegram et al., "Effect of erbB-2 (HER-2/neu) overexpression on chemotherapeutic drug sensitivity in human breast and ovarian cancer cells" Proceedings of the American Association for Cancer Research (Abstract No. 152) 34:26 (Mar. 1993).
Piccart and Kaufmann, "Introduction" European Journal of Cancer 37(Suppl. 1):S1-S2 (Jan. 2001).

Piccart et al., "HER2: a 'predictive factor' ready to use in the daily management of breast cancer patients?" European Journal of Cancer 36(14):1755-1761 (Sep. 2000).
Piccart, M., "Closing remarks and treatment guidelines" European Journal of Cancer 37(Suppl. 1):S30-S33 (Jan. 2001).
Pietras et al., "HER-2 tyrosine kinase pathway targets estrogen receptor and promotes hormone-independent growth in human breast cancer cells" Oncogene 10(12):2435-2446 (Jun. 15, 1995).
Pietras et al., "Heregulin promotes growth of human breast cancer cells with HER-2 (erb B2) recptors" Proceedings of the American Association for Cancer Research (Abstract No. 573) 34:96 (Mar. 1993).
Read et al., "Hormonal modulation of HER-2/neu protooncogene messenger ribonucleic acid and p185 protein expression in human breast cancer cell lines" Cancer Reserach 50(13):3947-3951 (Jul. 1, 1990).
Warri et al., "Estrogen suppression of erbB2 expression is associated with increased growth rate of ZR-75-1 human breast cancer cells in vitro and in nude mice" International Journal of Cancer 49(4):616-623 (Oct. 21, 1991).
Witters et al., "Enhanced anti-proliferative activity of the combination of tamoxifen plus HER-2-neu antibody" Breast Cancer Research & Treatment 42(1):1-5 (Jan. 1997).
"Are adjuvant Herceptin trials using the wrong drugs?" Scrip 2493:21 (Nov. 26, 1999).
Arteaga et al., "p185$^{c-erbB-2}$ Signaling Enhances Cisplatin-induced Cytotoxicity in Human Breast Carcinoma Cells: Association Between an Oncogenic Receptor Tyrosine Kinase and Drug-induced DNA Repair" Cancer Research 54(14):3758-3765 (Jul. 15, 1994).
Bacus et al., "Differentiation of Cultured Human Breast Cancer Cells (AU-565 and MCF-7) Associated With Loss of Cell Surface HER-2/neu Antigen" Molecular Carcinogenesis 3(6):350-362 (1990).
Bacus et al., "Tumor-inhibitory Monoclonal Antibodies to the HER-2/Neu Receptor Induce Differentiation of Human Breast Cancer Cells" Cancer Research 52(9):2580-2589 (May 1, 1992).
Baselga and Mendelsohn, "Receptor Blockade With Monoclonal Antibodies As Anti-Cancer Therapy" Pharmac. Ther. 64:127-154 (1994).
Baselga et al., "Anti HER2 Humanized Monoclonal Antibody (MAb) Alone and in Combination with Chemotherapy Against Human Breast Carcinoma Xenografts" Proceedings of ASCO-13th Annual Meeting (Abstract #53), Dallas, TX 13:63 (Mar. 1994).
Baselga et al., "Antitumor activity of paclitaxel in combination with anti-growth factor receptor monoclonal antibodies in breast cancer xenografts" Proceedings of the American Association for Cancer Research (Abstract No. 2262) 35:380 (Mar. 1994).
Baselga et al., "Antitumor effects of doxorubicin in combination with anti-epidermal growth factor receptor monoclonal antibodies" Journal of the National Cancer Institute 85(16):1327-1333 (Aug. 18, 1993).
Baselga et al., "HER2 Overexpression and Paclitaxel Sensitivity in Breast Cancer: Therapeutic Implications" Oncology (Supplement No. 2) 11(3):43-48 (Mar. 1997).
Baselga et al., "Monoclonal Antibodies Directed Against Growth Factor Receptors Enhance the Efficacy of Chemotherapeutic Agents." Annals of Oncology (abstract #010) 5(Suppl. 5) (1994).
Baselga et al., "Phase II Study of Weekly Intravenous Recombinant Humanized Anti-p185$^{HER2}$ Monoclonal Antibody in Patients With HER2/neu-Overexpressing Metastatic Breast Cancer" J. Clin. Oncol. 14(3):737-744 (Mar. 1996).
Baselga et al., "Recombinant Humanized Anti-HER2 Antibody (Herceptin) Enchances the Antitumor Activity of Paclitaxel and Doxorubicin against HER2/neu Overexpessing Human Breast Cancer Xenografts" Cancer Research 58:2825-2831 (Jul. 1998).
Bunn et al., "HER2/neu expression and effects of Herceptin alone and in combination with cytotoxic agents in lung cancer" Proceedings of the American Association for Cancer Research (Abstract No. 4571) 41:719 (Mar. 2000).
Burris et al., "Phase II trial of docetaxel and Herceptin(R) as First- or second-line chemotherapy for women with metastatic breast cancer whose tumours overexpress HER2" European Journal of Cancer (Abstract No. 1293) 35(4):S322 (Sep. 1999).

Carmichael et al., "Advanced breast cancer: a phase II trial with gemcitabine" *Journal of Clinical Oncology* 13(11):2731-2736 (Nov. 1995).

Carmichael et al., "Advanced breast cancer: investigational role of gemcitabine" *European Journal of Cancer* 33(Suppl. 1):S27-S30 (Jan. 1997).

Carter et al., "Humanization of an Anti-p185$^{HER2}$ Antibody For Human Cancer Therapy" *Proc. Natl. Acad. Sci. USA* 89:4285-4289 (May 1992).

Clemons et al., "Review of recent trials of chemotherapy for advanced Breast cancer: studies excluding taxanes" *European Journal of Cancer* 33(13):2171-2182 (Nov. 1997).

D'Souza and Taylor-Papadimitriou., "Overexpression of ERBB2 in Human Mammary Epithelial Cells Signals Inhibition of Transcription of the E-Cadherin Gene." *Proc. Natl. Acad. Sci. USA* 91(15):7202-7206 (Jul. 19, 1994).

Davidson, N., "Single-agent paclitaxel at first relapse following adjuvant chemotherapy for breast cancer" *Seminars in Oncology* 22(6 Suppl 14):2-6 (Dec. 1995).

De Santes et al., "Radiolabeled Antibody Targeting of the HER-2/neu Oncoprotein" *Cancer Research* 52:1916-1923 (1992).

Di Fiore et al., "erbB-2 Is A Potent Oncogene When Overexpressed In NIH/3T3 Cells." *Science* 237(4811):178-182 (Jul. 10, 1987).

Drebin et al., "Down-Modulation of an Oncogene Protein Product and Reversion of the Transformed Phenotype by Monoclonal Antibodies" *Cell* 41(3):695-706 (Jul. 1985).

Drebin et al., "Inhibition of Tumor Growth By a Monoclonal Antibody Reactive With an Oncogene-Encoded Tumor Antigen" *Proc. Natl. Acad. Sci.* 83:9129-9133 (1986).

Drebin et al., "Monoclonal Antibodies Reactive With Distinct Domains of the neu Oncogene-Encoded p185 Molecule Exert Synergistic Anti-Tumor Effects In Vivo" *Oncogene* 2:273-277 (1988).

Drebin et al., "Monoclonal Antibodies Specific for the neu Oncogene Product Directly Mediate Anti-tumor Effects In Vivo" *Oncogene* 2(4):387-394 (1988).

Fendly, B.M. et al., "Characterization of Murine Monoclonal Antibodies Reactive to Either the Human Epidermal Growth Factor Receptor or HER2/neu Gene Product" *Cancer Research* 50:1550-1558 (Mar. 1, 1990).

Fleiss, JL *Statistical Methods for Rates and Proportions*, 2nd edition, New York, NY:Wiley pp. 13-17 (1981).

Fornier et al., "Trastuzumab in combination with chemotherapy for the treatment of metastatic breast cancer" *Seminars in Oncology* 27(6 Suppl 11):38-45 (Dec. 2000).

Gatzemeier et al., "A randomised phase II study of gemcitabine/cisplatin alone and with Herceptin in patients with HER2-positive non-small cell lung cancer (NSCLC)" (Poster to be presented at the 2001 ECCO meeting).

Gemzar (gemcitabine HCL), "Product Information—PDR" (2000).

Green et al., "Preclinical Evaluation of WR-151327: An Orally Active Chemotherapy Protector" *Cancer Research* 54(3):738-741 (Feb. 1, 1994).

Guy et al., "Expression of the neu Protooncogene in the Mammary Epithelium of Transgenic Mice Induces Metastatic Disease." *Proc. Natl. Acad. Sci. USA* 89(22):10578-10582 (Nov. 15, 1992).

Hancock et al., "A Monoclonal Antibody Against the c-erbB-2 Protein Enhances the Cytotoxicity of cis-Diamminedichloroplatinum Against Human Breast and Ovarian Tumor Cell Lines" *Cancer Research* 51:4575-4580 (Sep. 1, 1991).

Hansen, H., "Gemcitabine—a review" *Annals of Oncology* (Abstract #058 from the 9th NCI-EORTC Symposium on New Drugs in Cancer Therapy held in Amsterdam on Mar. 12-15, 1996) 7(Suppl. 1):29 (1996).

Harwerth et al., "Monoclonal Antibodies Against the Extracellular Domain of the erbB-2 Receptor Function as Partial Ligand Agonists" *Journal of Biological Chemistry* 267(21):15160-15167 (Jul. 25, 1992).

"Herceptin (Trastuzumab)" *Product Information* (2000).

Hudziak et al., "Increased Expression of the Putative Growth Factor Receptor p185$^{HER2}$ Causes Transformation and Tumorigenesis of NIH 3T3 Cells." *Proc. Natl. Acad. Sci. USA* 84(20):7159-7163 (Oct. 1987).

Hudziak et al., "p185$^{HER2}$ Monoclonal Antibody Has Antiproliferative Effects In Vitro and Sensitizes Human Breast Tumor Cells to Tumor Necrosis Factor" *Molecular & Cellular Biology* 9(3):1165-1172 (Mar. 1989).

Hynes and Stern., "The Biology of erbB-2/neu/HER-2 and Its Role in Cancer." *Biochimica et Biophysica Acta* 1198(2-3):165-184 (Dec. 30, 1994).

Ilgen et al., "Characterization of anti-HER/2 antibodies which inhibit the growth of breast tumor cells in vitro" *Proceedings of the American Association for Cancer Research* (abstract #3209) 37:470 (Mar. 1996).

Kasprzyk et al., "Therapy of an Animal Model of Human Gastric Cancer Using a Combination of Anti-erbB-2 Monoclonal Antibodies" *Cancer Research* 52(10):2771-2776 (May 15, 1992).

Konecny et al., "Therapeutic advantage of chemotherapy drugs in combination with Herceptin against human breast cancer cells with HER-2/NEU overexpression" *Breast Cancer Res Treat* (Abstract No. 467) 57:114 (1999).

Kotts et al., "Differential Growth Inhibition of Human Carcinoma Cells Exposed to Monoclonal Antibodies Directed against the Extracellular Domain of the HER2/ERBB2 Protooncogene" *In Vitro* (Abstract #176) 26(3):59A (1990).

Kumar et al., "Regulation of Phosphorylation of the c-erbB-2/HER2 Gene Product by a Monoclonal Antibody and Serum Growth Factor(s) in Human Mammary Carcinoma Cells" *Molecular & Cellular Biology* 11(2):979-986 (Feb. 1991).

Lewis et al., "Differential Responses of Human Tumor Cell Lines to Anti-p185$^{HER2}$ Monoclonal Antibodies." *Cancer Immunol. Immunother.* 37:255-263 (1993).

Lewis et al., "Growth Regulation of Human Breast and Ovarian Tumor Cells by Heregulin: Evidence for the Requirement of ErbB2 as a Critical Component in Mediating Heregulin Responsiveness" *Cancer Research* 56:1457-1465 (Mar. 15, 1996).

Llombart et al., "Biweekly gemcitabine and paclitaxel in advanced breast cancer. Phase II trial and predictive value of HER2 extracellular domain (ECD)" *European Journal of Cancer* (Abstract No. 390) 36(Suppl 5):S121-S122 (Sep. 2000).

Maier et al., "Requirements for the Internalization of a Murine Monoclonal Antibody Directed against the HER-2/neu Gene Product c-erbB-2" *Cancer Research* 51(19):5361-5369 (Oct. 1, 1991).

Masui et al., "Growth Inhibition of Human Tumor Cells in Athymic Mice by Anti-Epidermal Growth Factor Receptor Monoclonal Antibodies" *Cancer Research* 44(3):1002-1007 (Mar. 1984).

Masuko et al., "A murine Monoclonal Antibody That Recognizes an Extracellular Domain of the Human c-erbB-2 Protooncogene Product" *Jpn J. Cancer Res.* 80:10-14 (Jan. 1989).

McCann et al., "c-erbB-2 Oncoprotein Expression in Primary Human Tumors" *Cancer* 65(1):88-92 (Jan. 1, 1990).

McKenzie et al., "Generation and Characterization of Monoclonal Antibodies Specific for the Human neu Oncogene Product, p185" *Oncogene* 4:543-548 (1989).

Mendelsohn et al., "Receptor Blockade and Chemotherapy: A New Approach to Combination Cancer therapy." *Annals of Oncology* (abstract #040) 7(Suppl. 1):22 (1996).

Miller et al., "Gemcitabine, paclitaxel, and trastuzumab in metastatic breast cancer" *Oncology* 15(2 Supp 3):38-40 (Feb. 2001).

Miller et al., "Phase II study of gemcitabine, paclitaxel and trastuzumab in metastatic breast cancer; a Hoosier Oncology Group trial" (Abstract #437. Presented at the 2002 SABCS meeting.) (2002).

Mosconi et al., "Combination therapy with gemcitabine in non-small cell lung cancer" *European Journal of Cancer* 33(Suppl. 1):S14-S17 (Jan. 1997).

Myers et al., "Biological Effects of Monoclonal Antireceptor Antibodies Reactive with neu Oncogene Product, p185neu" *Methods in Enzymology* 198:277-290 (1991).

Nagourney et al., "Trastuzumab (Herceptin) enhancement of cytotoxic drug activity in human tumor primary cultures" *Breast Cancer Res Treat* (Abstract No. 475) 57:116 (1999).

Nelson and Fry, "Inhibition of ERBB family receptors by CI-1033 enhances the cytotoxicity of gemcitabine via modulation of AKT and map kinases" *Proceedings of the American Association for Cancer Research* (Abstract No. 1533) 41:241 (Mar. 2000).

Norton, L., "Evolving Concepts in the Systemic Drug Therapy of Breast Cancer." *Seminars in Oncology* 24(4 Suppl 10):S10-3-S10-10 (Aug. 1997).

Pegram et al., "Inhibitory effects of combinations of HER-2/neu antibody and chemotherapeutic agents used for treatment of human breast cancers" *Oncogene* 18:2241-2251 (1999).

Pietras et al., "Antibody to HER-2/neu Receptor Blocks DNA Repair After Cisplatin in Human Breast and Ovarian Cancer Cells" *Oncogene* 9:1829-1838 (1994).

Raefsky et al., "Phase II Trial of Docetaxel and Herceptin as First- or Second-Line Chemotherapy for Women with Metastatic Breast Cancer Whose Tumors Overexpress HER2" *Proceedings of ASCO (Abstract #523)* 18:137a (1999).

Ravdin and Chamness, "The c-erbB-2 proto-oncogene as a prognostic and predictive marker in breast cancer: a paradigm for the development of other macromolecular markers—a review" *Gene* 159(1):19-27 (Jun. 14, 1995).

Rodeck et al., "Interactions between growth factor receptors and corresponding monoclonal antibodies in human tumors" *J. Cellular Biochem.* 35(4):315-320 (1987).

Safran et al., "Herceptin and gemcitabine for metastatic pancreatic cancers that overexpress HER-2/neu" *Proc. Am. Soc. Clin. Oncol.* (Abstract No. 517) 20:130A (2001).

Sarup et al., "Characterization of an Anti-P185$^{HER2}$ Monoclonal Antibody that Stimulates Receptor Function and Inhibits Tumor Cell Growth" *Growth Regulation* 1:72-82 (1991).

Schlom, J., "Monoclonal Antibodies: They're More and Less Than You Think" *Molecular Foundations of Oncology*, Broder, S. ed., Baltimore, MD:Williams & Wilkins, Chapter 6, pp. 95-134 (1991).

Scott et al., "p185$^{HER2}$ Signal Transduction in Breast Cancer Cells" *Journal of Biological Chemistry* 266(22):14300-14305 (Aug. 5, 1991).

Seidman et al., "Memorial Sloan-Kettering Cancer Center experience with paclitaxel in the treatment of breast cancer" *Seminars in Oncology* 22(5 Suppl 12):108-116 (Oct. 1995).

Seifert et al., "Dexrazoxane in the prevention of doxorubicin-induced cardiotoxicity" *Annals of Pharmacotherapy* 28(9):1063-1072 (Sep. 1994).

Shawver et al., "Ligand-Like Effects Induced by Anti-c-erbB-2 Antibodies Do Not Correlate with and Are Not Required for Growth Inhibition of Human Carcinoma Cells" *Cancer Research* 54(5):1367-1373 (Mar. 1, 1994).

Shepard et al., "Monoclonal Antibody Therapy of Human Cancer: Taking the HER2 Protooncogene to the Clinic" *J. Clin. Immunol.* 11(3):117-127 (1991).

Singal and Iliskovic, "Doxorubicin-induced cardiomyopathy" *New England J. of Medicine* 339(13):900-905 (Sep. 24, 1998).

Singal et al., "Combination therapy with probucol prevents adriamycin-induced cardiomyopathy" *Journal of Molecular & Cellular Cardiology* 27(4):1055-1063 (Apr. 1995).

Slamon et al., "Human Breast Cancer: Correlation of Relapse and Survival with Amplification of the HER-2/neu Oncogene" *Science* 235:177-182 (Jan. 9, 1987).

Slamon et al., "Studies of the HER-2/neu Proto-Oncogene in Human Breast and Ovarian Cancer" *Science* 244:707-712 (May 12, 1989).

Sliwkowski et al., "A humanized monoclonal antibody for the treatment of HER2 overexpressing breast cancer" *Proceedings of the American Association for Cancer Research* (abstract only) 37:625-626 (Mar. 1996).

Sliwkowski et al., "Coexpression of erbB2 and erbB3 Proteins Reconstitutes a High Affinity Receptor for Heregulin" *Journal of Biological Chemistry* 269(20):14661-14665 (May 20, 1994).

Stancovski et al., "Mechanistic Aspects of the Opposing Effects of Monoclonal Antibodies to the ERBB2 Receptor on Tumor Growth" *Proc. Natl. Acad. Sci. USA* 88(19):8691-8695 (Oct. 1, 1991).

Tagliabue et al., "Selection of Monoclonal Antibodies Which Induce Internalization and Phosphorylation of p185$^{HER2}$ and Growth Inhibition of Cells With HER2/NEU Gene Amplification" *International Journal of Cancer* 47(6):933-937 (Apr. 1, 1991).

Tsai et al., "Cytotoxic effects of gemcitabine-containing regimens against human non-small cell lung cancer cell lines which express different levels of p185$^{neu}$" *Cancer Research* 56(4):794-801 (Feb. 15, 1996).

van Moorsel et al., "Combination chemotherapy studies with gemcitabine" *Seminars in Oncology* 24(2 Suppl. 7):S7-17-S7-23 (Apr. 1997).

Vitetta and Uhr, "Monoclonal Antibodies as Agonists: An Expanded Role for Their Use in Cancer Therapy" *Cancer Research* 54(20):5301-5309 (Oct. 15, 1994).

Xu et al., "Antibody-Induced Growth Inhibition is Mediated Through Immunochemically and Functionally Distinct Epitopes on the Extracellular Domain of the c-erbB-2 (HER-2/neu) Gene Product p185" *International Journal of Cancer* 53(3):401-408 (Feb. 1, 1993).

Zhang et al., "Shared antigenic epitopes and pathobiological functions of anti-p185$^{her2/neu}$ monoclonal antibodies" *Experimental and Molecular Pathology* 67:15-25 (1999).

Zinner et al., "Cisplation and gemcitabine combined with Herceptin in patients (Pts) with HER2 overexpressing, untreated, advanced, non-small-cell lung cancer (NSCLC); a phase II trial" *Proc. Am. Clin. Oncol.* Abstract No. 1307) 20:328A (2001).

Buzdar et al., "Anastrozole, a potent and selective aromatase inhibitor, versus megestrol acetate in postmenopausal women with advanced breast cancer: results of overview analysis of two phase III trials" *Journal of Clinical Oncology* 14(7):2000-2011 (Jul. 1996).

Buzdar et al., "Fadrozole HCL (CGS-16949A) versus megestrol acetate treatment of postmenopausal patients with metastatic breast carcinoma: results of two randomized double blind controlled multiinstitutional trials" *Cancer* 77(12):2503-2513 (Jun. 15, 1996).

Dickman, S., "Antibodies stage a comeback in cancer treatment" *Science* 280(5367):1196-1197 (May 22, 1998).

Grant et al., "Comparison of antiangiogenic activities using paclitaxel (taxol) and docetaxel (taxotere)" *International Journal of Cancer* 104(1):121-129 (Mar. 10, 2003).

Kaye et al., "Phase II trials of docetaxel (Taxotere) in advanced ovarian cancer—an updated overview" *European Journal of Cancer* 33(13):2167-2170 (Nov. 1997).

Klijn et al., "Clinical breast cancer, new developments in selection and endocrine treatment of patients" *Journal of Steroid Biochemistry & Molecular Biology* 43(1-3):211-221 (Sep. 1992).

Merlin et al., "In vitro comparative evaluation of trastuzumab (Herceptin) combined with paclitaxel (Taxol) or docetaxel (Taxotere) in HER2-expressing human breast cancer cell lines" *Annals of Oncology* 13(11):1743-1748 (Nov. 2002).

Nallani et al., "Differences in the induction of cytochrome P450 3A4 by taxane anticancer drugs, docetaxel and paclitaxel, assessed employing primary human hepatocytes" *Cancer Chemotherapy & Pharmacology* 54:219-229 (Sep. 2004).

Santen and Harvey, "Use of aromatase inhibitors in breast carcinoma" *Endocrine-Related Cancer* 6(1):75-92 (Mar. 1999).

Untch et al., "Comparison of paclitaxel and docetaxel (Taxotere) in gynecologic and breast cancer cell lines with the ATP-cell viability assay" *Anti-Cancer Drugs* 5(1):24-30 (Feb. 1994).

Agus et al., "Clinical Activity in a Phase I Trial of HER-2-Targeted rhuMAb 2C4 (pertuzumab) in Patients with Advanced Solid Malignancies (AST)" *Proceedings of the American Association for Cancer Research* (Abstract No. 771) 22:192 (2003).

Agus et al., "Clinical Activity in a Phase I Trial of HER2-Targeted rhuMAb 2C4 (pertuzumab) in Patients with Advanced Solid Malignancies" (Slides presented at the 2003 ASCO Annual Meeting) pp. 1-32 (2003).

Gordon et al., "Clinical activity of pertuzumab (rhuMab 2C4) in advanced, refractory or recurrent ovarian cancer (OC), and the role of HER2 activation status" *Journal of Clinical Oncology* (Abstract #5051 from the 41st Annual Meeting of ASCO) 23(16S):467s (Jun. 1, 2005).

Gordon et al., "Clinical activity of pertuzumab (rhuMab 2C4) in advanced, refractory or recurrent ovarian cancer and the role of HER2 activation status" (Poster #5051 from the 41st Annual Meeting of the American Society of Clinical Oncology (ASCO)) (May 15, 2005).

Herzig and Herzig, "Medical Oncology" (website link: http://www.qualitysurgical.org/Chapter%2033.htm) pp. 1-11 (2006).

Marty et al., "Randomized Phase II Trial of the Efficacy and Saftey of Trastuzumab Combined with Docetaxel in Patients with Human Epidermal Growth Factor Receptor 2-Positive Metastatic Breast Cancer Administered As First-Line Treatment" *Journal of Clinical Oncology* 23(19):4265-4274 (Jul. 1, 2005).

Brodowicz et al., "Single-agent gemcitabine as second- and third-line treatment in metastatic breast cancer" *The Breast* 9:338-342 (2000).

Brufsky et al., "Phase II study of gemcitabine (Gem) and trastuzumab (T) combination therapy in first line metastatic breast cancer (MBC) patients (pts) with HER2 overexpression" *Journal of Clinical Oncology* (Abstract No. 10591) 24(18S) (Jun. 20, 2006).

Bunn et al., "Expression of Her-2/neu in human lung cancer cell lines by immunohistochemistry and fluorescence in situ hybridization and its relationship to in vitro cytotoxicity by trastuzumab and chemotherapeutic agents" *Clinical Cancer Research* 7(10):3239-3250 (Oct. 2001).

Christodoulou et al., "Combination of trastuzumab and gemcitabine as salvage treatment in metastatic breast cancer: The experience of the Hellenic Cooperative Oncology Group (HeCOG)" (Poster presented at the 39th Annual ASCO Meeting held in Chicago, Illinois; May 31-Jun. 3, 2003) (2003).

Christodoulou et al., "Gemcitabine and trastuzumab combination as salvage treatment in patients with HER2-positive metastatic breast cancer" *Proc Am Soc Clin Oncol* (Abstract No. 166) 22:42 (2003).

"equivocal" *The American Heritage Dictionary of the English Language* (Definition found on http://www.credoreference.com/entry/4085073) (2003).

Hirsch et al., "Preclinical studies of gemcitabine and trastuzumab in breast and lung cancer cell lines" *Clinical Breast Cancer* (abstract only) 3(Suppl 1):12-16 (May 2002).

Hirsch et al., "Preclinical studies of gemcitabine and trastuzumab in breast and lung cancer cell lines" *Clinical Breast Cancer* 3(Suppl 1):S12-S16 (May 2002).

Nogueras et al., "Pilot study of gemcitabine (G) plus trastuzumab (H) in metastatic breast cancer patients with erb-2 overexpression previously treated with anthracyclines (A) and taxanes (T)" *European Journal of Cancer* (Abstract No. 416) 4(Suppl):169 (Mar. 2006).

O'Shaughnessy et al., "Phase II study of trastuzumab plus gemcitabine in chemotherapy-pretreated patients with metastatic breast cancer" *Clinical Breast Cancer* 5(2):142-147 (Jun. 2004).

O'Shaughnessy et al., "Phase II trial of gemcitabine plus trastuzumab in metastatic breast cancer patients previously treated with chemotherapy: preliminary results" *Clinical Breast Cancer* (abstract only) 3(Suppl 1):17-20 (May 2002).

Peacock et al., "Phase II trial of gemcitabine plus trastuzumab in minimally pretreated HER2 overexpressing metastatic breast cancer" *Jouranl of Clinical Oncology* (Abstract No. 704) 23(16S Part I of II):54s (Jun. 1, 2005).

Pegram et al., "Phase II Study of Intravenous Recombinant Humanized Anti-p185 HER-2 Monoclonal Antibody (rhuMAb HER-2) Plus Cisplatin in Patients with HER-2/NEU Overexpressing Metastatic Breast Cancer" *Proceedings of the ASCO-31st Annual Meeting* (Abstract #124) 14:106 (1995).

Robert et al., "Phase III comparative study of trastuzumab and paclitaxel with and without carboplatin in patients with HER-2/neu positive advanced breast cancer" (Abstract #35. Presented at the 2002 SABCS meeting.) (2002).

Voskoglou-Nomikos et al., "Clinical predictive value of the in vitro cell line, human xenograft, and mouse allograft preclinical cancer models" *Clinical Cancer Research* 9(11):4227-4239 (Sep. 15, 2003).

Yardley et al., "Final results of the Minnie Pearl Cancer Research Network first-line trial of weekly paclitaxel/carboplatin/trastuzumab in metastatic breast cancer" (Abstract #439. Presented at the 2002 SABCS meeting.) (2002).

Cottin, et al., "Impairment of diastolic function during short-term anthracycline chemotherapy", Br. Heart J., 73:61-64, (1995).

Johnson, et al., "Relationships between drug activity in NCI preclinical in vitro and in vivo models and early clinical trials", British Journal of Cancer, 84(10): 1424-1431, (2001).

Lane, et al., "ErbB2 potentiates breast tumor proliferation through modulation of $p27^{Kip1}$-Cdk2 complex formation: Receptor overexpression does not determine growth dependency", Molecular and Cellular Biology, vol. 20, No. 9, pp. 3210-3223, (2000).

Osborne, et al., "Antagonism of chemotherapy-induced cytotoxicity for human breast cancer cells by antiestrogens", Journal of Clinical Oncology, vol. 7, No. 6, pp. 710-717, (1989).

Woods, C., et al., "Taxol-induced mitotic block triggers rapid onset of a p53-independent apoptotic pathway", Molecular Medicine, vol. 1, No. 5, pp. 506-526, (1995).

Woods, K., et al., "Antagonism between tamoxifen and doxorubicin in the MCF-7 human breast tumor cell line", Biochemical Pharmacology, vol. 47, No. 8, pp. 1449-1452, (1994).

* cited by examiner

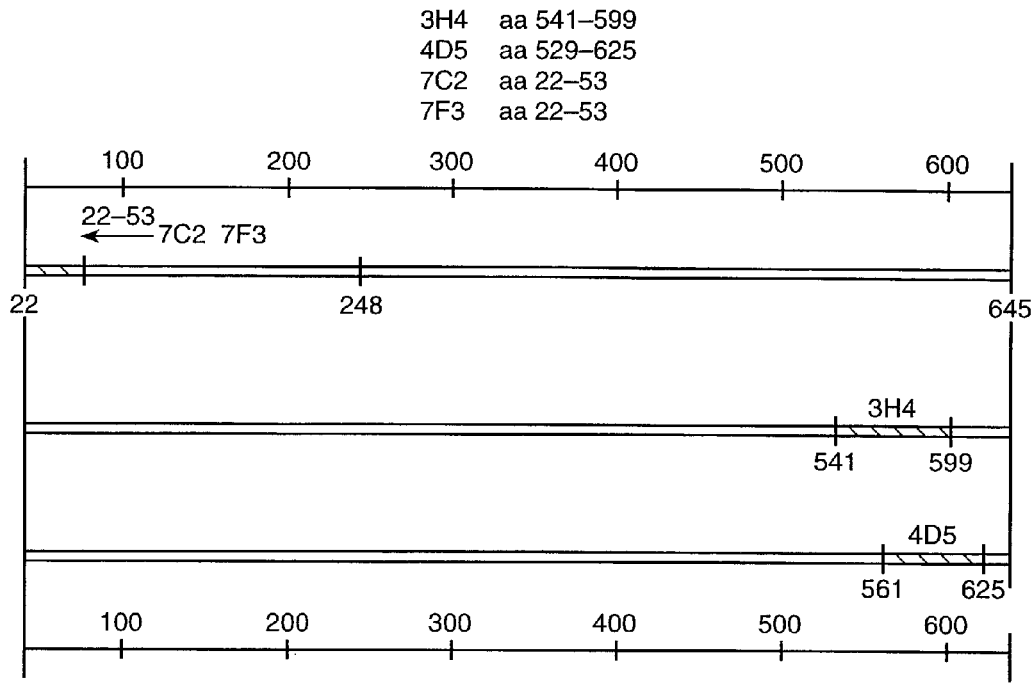

3H4 epitope (SEQ ID NO:8)

```
VEECRVLQGLPREYVNARHCLPCHPECQPQNGSVTCFGPEADQCVACAHYKDPPFCVAR
|                                                         |
541                                                       599
```

4D5 epitope (SEQ ID NO:9)

```
LPCHPECQPQNGSVTCFGPEADQCVACAHYKDPPFCVARCPSGVKPDLSYMPIWKFPDEEGACQP
|                                                               |
561                                                             625
```

FIG._1

```
1    MELAALCRWGLLLALLPPGAASTQVCTGTDMKLRLPA
38   SPETHLDMLRHLYQGCQVVQGNLELTYLPTNASLSFL
75   QDIQEVQGYVLIAHNQVRQVPLQRLRIVRGTQLFEDN
112  YALAVLDNGDPLNNTTPVTGASPGGLRELQLRSLTEI
149  LKGGVLIQRNPQLCYQDTILWKDIFHKNNQLALTLID
186  TNRSRA
```

FIG._2

SEQUENCE LISTING

<160> NUMBER OF SEQ ID NOS: 9

<210> SEQ ID NO 1
<211> LENGTH: 166
<212> TYPE: PRT
<213> ORGANISM: Homo sapiens

<400> SEQUENCE: 1

```
Cys Thr Gly Thr Asp Met Lys Leu Arg Leu Pro Ala Ser Pro Glu
 1               5                  10                  15

Thr His Leu Asp Met Leu Arg His Leu Tyr Gln Gly Cys Gln Val
                20                  25                  30

Val Gln Gly Asn Leu Glu Leu Thr Tyr Leu Pro Thr Asn Ala Ser
                35                  40                  45

Leu Ser Phe Leu Gln Asp Ile Gln Glu Val Gln Gly Tyr Val Leu
                50                  55                  60

Ile Ala His Asn Gln Val Arg Gln Val Pro Leu Gln Arg Leu Arg
                65                  70                  75

Ile Val Arg Gly Thr Gln Leu Phe Glu Asp Asn Tyr Ala Leu Ala
                80                  85                  90

Val Leu Asp Asn Gly Asp Pro Leu Asn Asn Thr Thr Pro Val Thr
                95                 100                 105

Gly Ala Ser Pro Gly Gly Leu Arg Glu Leu Gln Leu Arg Ser Leu
               110                 115                 120

Thr Glu Ile Leu Lys Gly Gly Val Leu Ile Gln Arg Asn Pro Gln
               125                 130                 135

Leu Cys Tyr Gln Asp Thr Ile Leu Trp Lys Asp Ile Phe His Lys
               140                 145                 150

Asn Asn Gln Leu Ala Leu Thr Leu Ile Asp Thr Asn Arg Ser Arg
               155                 160                 165
```

```
Ala
166

<210> SEQ ID NO 2
<211> LENGTH: 32
<212> TYPE: PRT
<213> ORGANISM: Homo sapiens

<400> SEQUENCE: 2

Ser Thr Gln Val Cys Thr Gly Thr Asp Met Lys Leu Arg Leu Pro
  1               5                  10                  15

Ala Ser Pro Glu Thr His Leu Asp Met Leu Arg His Leu Tyr Gln
                 20                  25                  30

Gly Cys
     32

<210> SEQ ID NO 3
<211> LENGTH: 11
<212> TYPE: PRT
<213> ORGANISM: Homo sapiens

<400> SEQUENCE: 3

Pro Lys Asn Ser Ser Met Ile Ser Asn Thr Pro
  1               5                  10  11

<210> SEQ ID NO 4
<211> LENGTH: 7
<212> TYPE: PRT
<213> ORGANISM: Homo sapiens

<400> SEQUENCE: 4

His Gln Ser Leu Gly Thr Gln
  1               5       7

<210> SEQ ID NO 5
<211> LENGTH: 8
<212> TYPE: PRT
<213> ORGANISM: Homo sapiens

<400> SEQUENCE: 5

His Gln Asn Leu Ser Asp Gly Lys
  1               5           8

<210> SEQ ID NO 6
<211> LENGTH: 8
<212> TYPE: PRT
<213> ORGANISM: Homo sapiens

<400> SEQUENCE: 6

His Gln Asn Ile Ser Asp Gly Lys
  1               5           8

<210> SEQ ID NO 7
<211> LENGTH: 8
<212> TYPE: PRT
<213> ORGANISM: Homo sapiens

<400> SEQUENCE: 7

Val Ile Ser Ser His Leu Gly Gln
  1               5           8

<210> SEQ ID NO 8
<211> LENGTH: 59
```

-continued

```
<212> TYPE: PRT
<213> ORGANISM: Homo sapiens

<400> SEQUENCE: 8

Val Glu Glu Cys Arg Val Leu Gln Gly Leu Pro Arg Glu Tyr Val
 1               5                  10                  15

Asn Ala Arg His Cys Leu Pro Cys His Pro Glu Cys Gln Pro Gln
                20                  25                  30

Asn Gly Ser Val Thr Cys Phe Gly Pro Glu Ala Asp Gln Cys Val
                35                  40                  45

Ala Cys Ala His Tyr Lys Asp Pro Pro Phe Cys Val Ala Arg
                50                  55              59

<210> SEQ ID NO 9
<211> LENGTH: 65
<212> TYPE: PRT
<213> ORGANISM: Homo sapiens

<400> SEQUENCE: 9

Leu Pro Cys His Pro Glu Cys Gln Pro Gln Asn Gly Ser Val Thr
 1               5                  10                  15

Cys Phe Gly Pro Glu Ala Asp Gln Cys Val Ala Cys Ala His Tyr
                20                  25                  30

Lys Asp Pro Pro Phe Cys Val Ala Arg Cys Pro Ser Gly Val Lys
                35                  40                  45

Pro Asp Leu Ser Tyr Met Pro Ile Trp Lys Phe Pro Asp Glu Glu
                50                  55                  60

Gly Ala Cys Gln Pro
                65
```

TREATMENT WITH ANTI-ERBB2 ANTIBODIES

This is a continuation of non-provisional application Ser. No. 09/208,649, filed Dec. 10, 1998, which claims priority under 35 USC §119 to provisional application No. 60/069,346, filed Dec. 12, 1997, the entire disclosures of which are hereby incorporated by reference.

FIELD OF THE INVENTION

The present invention concerns the treatment of disorders characterized by the overexpression of ErbB2. More specifically, the invention concerns the treatment of human patients susceptible to or diagnosed with cancer overexpressing ErbB2 with a combination of an anti-ErbB2 antibody and a chemotherapeutic agent other than an anthracycline, e.g. doxorubicin or epirubicin.

BACKGROUND OF THE INVENTION

Proto-oncogenes that encode growth factors and growth factor receptors have been identified to play important roles in the pathogenesis of various human malignancies, including breast cancer. It has been found that the human ErbB2 gene (erbB2, also known as her2, or c-erbB-2), which encodes a 185-kd transmembrane glycoprotein receptor (p185$^{HER2}$) related to the epidermal growth factor receptor (EGFR), is overexpressed in about 25% to 30% of human breast cancer (Slamon et al., *Science* 235:177-182 [1987]; Slamon et al., *Science* 244:707-712[1989]).

Several lines of evidence support a direct role for ErbB2 in the pathogenesis and clinical aggressiveness of ErbB2-overexpressing tumors. The introduction of ErbB2 into non-neoplastic cells has been shown to cause their malignant transformation (Hudziak et al., *Proc. Natl. Acad. Sci. USA* 84:7159-7163 [1987]; DiFiore et al., *Science* 237:178-182 [1987]). Transgenic mice that express HER2 were found to develop mammary tumors (Guy et al., *Proc. Natl. Acad. Sci. USA* 89:10578-10582 [1992]).

Antibodies directed against human erbB2 protein products and proteins encoded by the rat equivalent of the erbB2 gene (neu) have been described. Drebin et al., *Cell* 41:695-706 (1985) refer to an IgG2a monoclonal antibody which is directed against the rat neu gene product. This antibody called 7.16.4 causes down-modulation of cell surface p185 expression on B 104-1-1 cells (NIH-3T3 cells transfected with the neu proto-oncogene) and inhibits colony formation of these cells. In Drebin et al *PNAS* (USA) 83:9129-9133 (1986), the 7.16.4 antibody was shown to inhibit the tumorigenic growth of neu-transformed NIH-3T3 cells as well as rat neuroblastoma cells (from which the neu oncogene was initially isolated) implanted into nude mice. Drebin et al. in *Oncogene* 2:387-394 (1988) discuss the production of a panel of antibodies against the rat neu gene product. All of the antibodies were found to exert a cytostatic effect on the growth of neu-transformed cells suspended in soft agar. Antibodies of the IgM, IgG2a and IgG2b isotypes were able to mediate significant in vitro lysis of neu-transformed cells in the presence of complement, whereas none of the antibodies were able to mediate high levels of antibody-dependent cellular cytotoxicity (ADCC) of the neu-transformed cells. Drebin et al. *Oncogene* 2:273-277 (1988) report that mixtures of antibodies reactive with two distinct regions on the p185 molecule result in synergistic anti-tumor effects on neu-transformed NIH-3T3 cells implanted into nude mice. Biological effects of anti-neu antibodies are reviewed in Myers et al., *Meth. Enzym.* 198:277-290 (1991). See also WO94/22478 published Oct. 13, 1994.

Hudziak et al., *Mol. Cell. Biol.* 9(3):1165-1172 (1989) describe the generation of a panel of anti-ErbB2 antibodies which were characterized using the human breast tumor cell line SKBR3. Relative cell proliferation of the SKBR3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel, including 7C2 and 7F3, reduced cellular proliferation to a lesser extent in this assay. Hudziak et al. conclude that the effect of the 4D5 antibody on SKBR3 cells was cytostatic rather than cytotoxic, since SKBR3 cells resumed growth at a nearly normal rate following removal of the antibody from the medium. The antibody 4D5 was further found to sensitize p185$^{erbB2}$-overexpressing breast tumor cell lines to the cytotoxic effects of TNF-α. See also WO89/06692 published Jul. 27, 1989. The anti-ErbB2 antibodies discussed in Hudziak et al. are further characterized in Fendly et al. *Cancer Research* 50:1550-1558 (1990); Kotts et al In Vitro 26(3):59A (1990); Sarup et al. *Growth Regulation* 1:72-82 (1991); Shepard et al. *J. Clin. Immunol.* 11(3):117-127 (1991); Kumar et al. *Mol. Cell. Biol.* 11(2): 979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); and D'souza et al. *Proc. Nail Acad. Sci.* 91:7202-7206 (1994).

Tagliabue et al. *Int. J. Cancer* 47:933-937 (1991) describe two antibodies which were selected for their reactivity on the lung adenocarcinoma cell line (Calu-3) which overexpresses ErbB2. One of the antibodies, called MGR3, was found to internalize, induce phosphorylation of ErbB2, and inhibit tumor cell growth in vitro.

McKenzie et al. *Oncogene* 4:543-548 (1989) generated a panel of anti-ErbB2 antibodies with varying epitope specificities, including the antibody designated TA1. This TA1 antibody was found to induce accelerated endocytosis of ErbB2 (see Maier et al. *Cancer Res.* 51:5361-5369[1991]). Bacus et al. *Molecular Carcinogenesis* 3:350-362 (1990) reported that the TA1 antibody induced maturation of the breast cancer cell lines AU-565 (which overexpresses the erbB2 gene) and MCF-7 (which does not). Inhibition of growth and acquisition of a mature phenotype in these cells was found to be associated with reduced levels of ErbB2 receptor at the cell surface and transient increased levels in the cytoplasm.

Stancovski et al. *PNAS* (USA) 88:8691-8695 (1991) generated a panel of anti-ErbB2 antibodies, injected them i.p. into nude mice and evaluated their effect on tumor growth of murine fibroblasts transformed by overexpression of the erbB2 gene. Various levels of tumor inhibition were detected for four of the antibodies, but one of the antibodies (N28) consistently stimulated tumor growth. Monoclonal antibody N28 induced significant phosphorylation of the ErbB2 receptor, whereas the other four antibodies generally displayed low or no phosphorylation-inducing activity. The effect of the anti-ErbB2 antibodies on proliferation of SKBR3 cells was also assessed. In this SKBR3 cell proliferation assay, two of the antibodies (N12 and N29) caused a reduction in cell proliferation relative to control. The ability of the various antibodies to induce cell lysis in vitro via complement-dependent cytotoxicity (CDC) and antibody-mediated cell-dependent cytotoxicity (ADCC) was assessed, with the authors of this paper concluding that the inhibitory function of the antibodies was not attributed significantly to CDC or ADCC.

Bacus et al. *Cancer Research* 52:2580-2589 (1992) further characterized the antibodies described in Bacus et al. (1990) and Stancovski et al. of the preceding paragraphs. Extending the i.p. studies of Stancovski et al., the effect of the antibodies after i.v. injection into nude mice harboring mouse fibroblasts overexpressing human ErbB2 was assessed. As observed in their earlier work, N28 accelerated tumor growth whereas N12 and N29 significantly inhibited growth of the ErbB2-expressing cells. Partial tumor inhibition was also observed with the N24 antibody. Bacus et al. also tested the ability of the antibodies to promote a mature phenotype in the human breast cancer cell lines AU-565 and MDA-MB453 (which overexpress ErbB2) as well as MCF-7 (containing low levels of the receptor). Bacus et al. saw a correlation between tumor inhibition in vivo and cellular differentiation; the tumor-stimulatory antibody N28 had no effect on differentiation, and the tumor inhibitory action of the N12, N29 and N24 antibodies correlated with the extent of differentiation they induced.

Xu et al. *Int. J. Cancer* 53:401-408 (1993) evaluated a panel of anti-ErbB2 antibodies for their epitope binding specificities, as well as their ability to inhibit anchorage-independent and anchorage-dependent growth of SKBR3 cells (by individual antibodies and in combinations), modulate cell-surface ErbB2, and inhibit ligand stimulated anchorage-independent growth. See also WO94/00136 published Jan. 6, 1994 and Kasprzyk et al. *Cancer Research* 52:2771-2776 (1992) concerning anti-ErbB2 antibody combinations. Other anti-ErbB2 antibodies are discussed in Hancock et al. *Cancer Res.* 51:4575-4580 (1991); Shawver et al. *Cancer Res.* 54:1367-1373 (1994); Arteaga et al. *Cancer Res.* 54:3758-3765 (1994); and Harwerth et al. *J Biol. Chem.* 267:15160-15167 (1992).

A recombinant humanized anti-ErbB2 monoclonal antibody (a humanized version of the murine anti-ErbB2 antibody 4D5, referred to as rhuMAb HER2 or HERCEPTIN®) has been clinically active in patients with ErbB2-overexpressing metastatic breast cancers that had received extensive prior anti-cancer therapy (Baselga et al., *J. Clin. Oncol.* 14:737-744 [1996]).

ErbB2 overexpression is commonly regarded as a predictor of a poor prognosis, especially in patients with primary disease that involves axillary lymph nodes (Slamon et al., [1987] and [1989], supra Ravdin and Chamness, *Gene* 159:19-27 [1995]; and Hynes and Stern, *Biochim Biophys Acta* 1198: 165-184 [1994]), and has been linked to sensitivity and/or resistance to hormone therapy and chemotherapeutic regimens, including CMF (cyclophosphamide, methotrexate, and fluoruracil) and anthracyclines (Baselga et al., *Oncology* 11(3 Suppl 2):43-48 [1997]). However, despite the association of ErbB2 overexpression with poor prognosis, the odds of HER2-positive patients responding clinically to treatment with taxanes were greater than three times those of HER2-negative patients (Ibid). rhuMab HER2 was shown to enhance the activity of paclitaxel (TAXOL®) and doxorubicin against breast cancer xenografts in nude mice injected with BT-474 human breast adenocarcinoma cells, which express high levels of HER2 (Baselga et al., *Breast Cancer, Proceedings of ASCO*, Vol. 13, Abstract 53 [1994]).

SUMMARY OF THE INVENTION

The present invention concerns the treatment of disorders characterized by overexpression of ErbB2, and is based on the recognition that while treatment with anti-ErbB2 antibodies markedly enhances the clinical benefit of the use of chemotherapeutic agents in general, a syndrome of myocardial dysfunction that has been observed as a side-effect of anthracycline derivatives is increased by the administration of anti-ErbB2 antibodies.

Accordingly, the invention concerns a method for the treatment of a human patient susceptible to or diagnosed with a disorder characterized by overexpression of ErbB2 receptor comprising administering a therapeutically effective amount of a combination of an anti-ErbB2 antibody and a chemotherapeutic agent other than an anthracycline derivative, e.g. doxorubicin or epirubicin, in the absence of an anthracycline derivative, to the human patient.

The disorder preferably is a benign or malignant tumor characterized by the overexpression of the ErbB2 receptor, e.g. a cancer, such as, breast cancer, squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer. The chemotherapeutic agent preferably is a taxoid, such as TAXOL® (paclitaxel) or a TAXOL® derivative.

Although an antiproliferative effect is sufficient, in a preferred embodiment, the anti-ErbB2 antibody is capable of inducing cell death or is capable of inducing apoptosis. Preferred anti-ErbB2 antibodies bind the extracellular domain of the ErbB2 receptor, and preferably bind to the epitope 4D5 or 3H4 within the ErbB2 extracellular domain sequence. More preferably, the antibody is the antibody 4D5, most preferably in a humanized form.

The method of the present invention is particularly suitable for the treatment of breast or ovarian cancer, characterized by the overexpression of the ErbB2 receptor.

In another aspect, the invention concerns an article of manufacture, comprising a container, a composition within the container comprising an anti-ErbB2 antibody, optionally a label on or associated with the container that indicates that the composition can be used for treating a condition characterized by overexpression of ErbB2 receptor, and a package insert containing instructions to avoid the use of anthracycline-type chemotherapeutics in combination with the composition.

BRIEF DESCRIPTION OF THE DRAWINGS

FIG. 1 shows epitope-mapping of the extracellular domain of ErbB2 as determined by truncation mutant analysis and site-directed mutagenesis (Nakamura et al. *J. of Virology* 67(10):6179-6191 [October 1993]; Renz et al. *J. Cell Biol.* 125(6):1395-1406 [June 1994]). The anti-proliferative MAbs 4D5 and 3H4 bind adjacent to the transmembrane domain. The various ErbB2-ECD truncations or point mutations were prepared from cDNA using polymerase chain reaction technology. The ErbB2 mutants were expressed as gD fusion proteins in a mammalian expression plasmid. This expression plasmid uses the cytomegalovirus promoter/enhancer with SV40 termination and polyadenylation signals located downstream of the inserted cDNA. Plasmid DNA was transfected into 293S cells. One day following transfection, the cells were metabolically labeled overnight in methionine and cysteine-free, low glucose DMEM containing 1% dialyzed fetal bovine serum and 25 µCi each of $^{35}S$ methionine and $^{35}S$ cysteine. Supernatants were harvested either the ErbB2 MAbs or control antibodies were added to the supernatant and incubated 2-4 hours at 4° C. The complexes were precipitated, applied to a 10-20% Tricine SDS gradient gel and electrophoresed at 100 V. The gel was electroblotted onto a membrane and analyzed by autoradiography. SEQ ID NOs:8 and 9 depict the 3H4 and 4D5 epitopes, respectively.

FIG. 2 depicts with underlining the amino acid sequence of Domain 1 of ErbB2 (SEQ ID NO: 1). Bold amino acids indicate the location of the epitope recognized by MAbs 7C2 and 7F3 as determined by deletion mapping, i.e. the "7C2/7F3 epitope" (SEQ ID NO:2).

DETAILED DESCRIPTION OF THE PREFERRED EMBODIMENTS

I. Definitions

The terms "HER2", "ErbB2" "c-Erb-B2" are used interchangeably. Unless indicated otherwise, the terms "ErbB2" "c-Erb-B2" and "HER2" when used herein refer to the human protein and "her2", "erbB2" and "c-erb-B2" refer to human gene. The human erbB2 gene and ErbB2 protein are, for example, described in Semba et al., *PNAS* (USA) 82:6497-6501 (1985) and Yamamoto et al. *Nature* 319:230-234 (1986) (Genebank accession number X03363). ErbB2 comprises four domains (Domains 1-4).

The "epitope 4D5" is the region in the extracellular domain of ErbB2 to which the antibody 4D5 (ATCC CRL 10463) binds. This epitope is close to the transmembrane region of ErbB2. To screen for antibodies which bind to the 4D5 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed (see FIG. 1) to assess whether the antibody binds to the 4D5 epitope of ErbB2 (i.e. any one or more residues in the region from about residue 529, e.g. about residue 561 to about residue 625, inclusive).

The "epitope 3H4" is the region in the extracellular domain of ErbB2 to which the antibody 3H4 binds. This epitope is shown in FIG. 1, and includes residues from about 541 to about 599, inclusive, in the amino acid sequence of ErbB2 extracellular domain.

The "epitope 7C2/7F3" is the region at the N terminus of the extracellular domain of ErbB2 to which the 7C2 and/or 7F3 antibodies (each deposited with the ATCC, see below) bind. To screen for antibodies which bind to the 7C2/7F3 epitope, a routine cross-blocking assay such as that described in *Antibodies, A Laboratory Manual*, Cold Spring Harbor Laboratory, Ed Harlow and David Lane (1988), can be performed. Alternatively, epitope mapping can be performed to establish whether the antibody binds to the 7C2/7F3 epitope on ErbB2 (i.e. any one or more of residues in the region from about residue 22 to about residue 53 of ErbB2; SEQ ID NO:2).

The term "induces cell death" or "capable of inducing cell death" refers to the ability of the antibody to make a viable cell become nonviable. The "cell" here is one which expresses the ErbB2 receptor, especially where the cell overexpresses the ErbB2 receptor. A cell which "overexpresses" ErbB2 has significantly higher than normal ErbB2 levels compared to a noncancerous cell of the same tissue type. Preferably, the cell is a cancer cell, e.g. a breast, ovarian, stomach, endometrial, salivary gland, lung, kidney, colon, thyroid, pancreatic or bladder cell. In vitro, the cell may be a SKBR3, BT474, Calu 3, MDA-MB-453, MDA-MB-361 or SKOV3 cell. Cell death in vitro may be determined in the absence of complement and immune effector cells to distinguish cell death induced by antibody dependent cellular cytotoxicity (ADCC) or complement dependent cytotoxicity (CDC). Thus, the assay for cell death may be performed using heat inactivated serum (i.e. in the absence of complement) and in the absence of immune effector cells. To determine whether the antibody is able to induce cell death, loss of membrane integrity as evaluated by uptake of propidium iodide (PI), trypan blue (see Moore et al. *Cytotechnology* 17:1-11 [1995]) or 7AAD can be assessed relative to untreated cells. Preferred cell death-inducing antibodies are those which induce P1 uptake in the "P1 uptake assay in BT474 cells".

The phrase "induces apoptosis" or "capable of inducing apoptosis" refers to the ability of the antibody to induce programmed cell death as determined by binding of annexin V, fragmentation of DNA, cell shrinkage, dilation of endoplasmic reticulum, cell fragmentation, and/or formation of membrane vesicles (called apoptotic bodies). The cell is one which overexpresses the ErbB2 receptor. Preferably the "cell" is a tumor cell, e.g. a breast, ovarian, stomach, endometrial, salivary gland, lung, kidney, colon, thyroid, pancreatic or bladder cell. In vitro, the cell may be a SKBR3, BT474, Calu 3 cell, MDA-MB-453, MDA-MB-361 or SKOV3 cell. Various methods are available for evaluating the cellular events associated with apoptosis. For example, phosphatidyl serine (PS) translocation can be measured by annexin binding; DNA fragmentation can be evaluated through DNA laddering as disclosed in the example herein; and nuclear/chromatin condensation along with DNA fragmentation can be evaluated by any increase in hypodiploid cells. Preferably, the antibody which induces apoptosis is one which results in about 2 to 50 fold, preferably about 5 to 50 fold, and most preferably about 10 to 50 fold, induction of annexin binding relative to untreated cell in an "annexin binding assay using BT474 cells" (see below).

Sometimes the pro-apoptotic antibody will be one which blocks HRG binding/activation of the ErbB2/ErbB3 complex (e.g. 7F3 antibody). In other situations, the antibody is one which does not significantly block activation of the ErbB2/ErbB3 receptor complex by HRG (e.g. 7C2). Further, the antibody may be one like 7C2 which, while inducing apoptosis, does not induce a large reduction in the percent of cells in S phase (e.g. one which only induces about 0-10% reduction in the percent of these cells relative to control).

The antibody of interest may be one like 7C2 which binds specifically to human ErbB2 and does not significantly cross-react with other proteins such as those encoded by the erbB1, erbB3 and/or erbB4 genes. Sometimes, the antibody may not significantly cross-react with the rat neu protein, e.g., as described in Schecter et al. *Nature* 312:513 (1984) and Drebin et al., *Nature* 312:545-548 (1984). In such embodiments, the extent of binding of the antibody to these proteins (e.g., cell surface binding to endogenous receptor) will be less than about 10% as determined by fluorescence activated cell sorting (FACS) analysis or radioimmunoprecipitation (RIA).

"Heregulin" (HRG) when used herein refers to a polypeptide which activates the ErbB2-ErbB3 and ErbB2-ErbB4 protein complexes (i.e. induces phosphorylation of tyrosine residues in the complex upon binding thereto). Various heregulin polypeptides encompassed by this term are disclosed in Holmes et al., *Science*, 256:1205-1210 (1992); WO 92/20798; Wen et al., *Mol. Cell. Biol.*, 14(3):1909-1919 (1994); and Marchionni et al., *Nature*, 362:312-318 (1993), for example. The term includes biologically active fragments and/or variants of a naturally occurring HRG polypeptide, such as an EGF-like domain fragment thereof (e.g. $HRG\beta1_{177-244}$).

The "ErbB2-ErbB3 protein complex" and "ErbB2-ErbB4 protein complex" are noncovalently associated oligomers of the ErbB2 receptor and the ErbB3 receptor or ErbB4 receptor, respectively. The complexes form when a cell expressing both of these receptors is exposed to HRG and can be isolated by immunoprecipitation and analyzed by SDS-PAGE as described in Sliwkowski et al., *J. Biol. Chem.*, 269(20): 14661-14665 (1994).

"Antibodies" (Abs) and "immunoglobulins" (Igs) are glycoproteins having the same structural characteristics. While antibodies exhibit binding specificity to a specific antigen, immunoglobulins include both antibodies and other antibody-like molecules which lack antigen specificity. Polypeptides of the latter kind are, for example, produced at low levels by the lymph system and at increased levels by myelomas.

"Native antibodies" and "native immunoglobulins" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light-chain variable domain is aligned with the variable domain of the heavy chain. Particular amino acid residues are believed to form an interface between the light- and heavy-chain variable domains.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called complementarity-determining regions (CDRs) or hypervariable regions both in the light-chain and the heavy-chain variable domains. The more highly conserved portions of variable domains are called the framework region (FR). The variable domains of native heavy and light chains each comprise four FR regions, largely adopting a β-sheet configuration, connected by three CDRs, which form loops connecting, and in some cases forming part of, the β-sheet structure. The CDRs in each chain are held together in close proximity by the FRs and, with the CDRs from the other chain, contribute to the formation of the antigen-binding site of antibodies (see Kabat et al., *NIH Publ. No.* 91-3242, Vol. 1, pages 647-669 [1991]). The constant domains are not involved directly in binding an antibody to an antigen, but exhibit various effector functions, such as participation of the antibody in antibody dependent cellular cytotoxicity.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-recognition and -binding site. This region consists of a dimer of one heavy- and one light-chain variable domain in tight, non-covalent association. It is in this configuration that the three CDRs of each variable domain interact to define an antigen-binding site on the surface of the $V_H$-$V_L$ dimer. Collectively, the six CDRs confer antigen-binding specificity to the antibody. However, even a single variable domain (or half of an Fv comprising only three CDRs specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The "light chains" of antibodies (immunoglobulins) from any vertebrate species can be assigned to one of two clearly distinct types, called kappa (κ) and lambda (λ), based on the amino acid sequences of their constant domains.

Depending on the amino acid sequence of the constant domain of their heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA, and IgA2. The heavy-chain constant domains that correspond to the different classes of immunoglobulins are called α, δ, ε, γ, and μ, respectively. The subunit structures and three-dimensional configurations of different classes of immunoglobulins are well known.

The term "antibody" is used in the broadest sense and specifically covers intact monoclonal antibodies, polyclonal antibodies, multispecific antibodies (e.g. bispecific antibodies) formed from at least two intact antibodies, and antibody fragments so long as they exhibit the desired biological activity.

"Antibody fragments" comprise a portion of an intact antibody, preferably the antigen binding or variable region of the intact antibody. Examples of antibody fragments include Fab, Fab', F(ab')$_2$, and Fv fragments; diabodies; linear antibodies (Zapata et al. *Protein Eng.* 8(10):1057-1062 [1995]); single-chain antibody molecules; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., *Nature*, 256:495 (1975), or may be made by recombinant DNA methods (see, e.g., U.S. Pat. No. 4,816,567). The "monoclonal antibodies"

may also be isolated from phage antibody libraries using the techniques described in Clackson et al., *Nature,* 352:624-628 (1991) and Marks et al., *J. Mol. Biol.,* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 [1984]).

"Humanized" forms of non-human (e.g., murine) antibodies are chimeric immunoglobulins, immunoglobulin chains or fragments thereof (such as Fv, Fab, Fab', F(ab')$_2$ or other antigen-binding subsequences of antibodies) which contain minimal sequence derived from non-human immunoglobulin. For the most part, humanized antibodies are human immunoglobulins (recipient antibody) in which residues from a complementarity determining region (CDR) of the recipient are replaced by residues from a CDR of a non-human species (donor antibody) such as mouse, rat or rabbit having the desired specificity, affinity, and capacity. In some instances, Fv framework region (FR) residues of the human immunoglobulin are replaced by corresponding non-human residues. Furthermore, humanized antibodies may comprise residues which are found neither in the recipient antibody nor in the imported CDR or framework sequences. These modifications are made to further refine and maximize antibody performance. In general, the humanized antibody will comprise substantially all of at least one, and typically two, variable domains, in which all or substantially all of the CDRs correspond to those of a non-human immunoglobulin and all or substantially all of the FRs are those of a human immunoglobulin sequence. The humanized antibody optimally also will comprise at least a portion of an immunoglobulin constant region (Fc), typically that of a human immunoglobulin. For further details, see Jones et al., *Nature,* 321:522-525 (1986); Reichmann et al., *Nature,* 332:323-329 (1988); and Presta, *Curr. Op. Struct. Biol.,* 2:593-596 (1992). The humanized antibody includes a PRIMATIZED™ antibody wherein the antigen-binding region of the antibody is derived from an antibody produced by immunizing macaque monkeys with the antigen of interest.

"Single-chain Fv" or "sFv" antibody fragments comprise the $V_H$ and $V_L$ domains of antibody, wherein these domains are present in a single polypeptide chain. Preferably, the Fv polypeptide further comprises a polypeptide linker between the $V_H$ and $V_L$ domains which enables the sFv to form the desired structure for antigen binding. For a review of sFv see Plückthun in *The Pharmacology of Monoclonal Antibodies,* vol. 113, Rosenburg and Moore eds., Springer-Verlag, New York, pp. 269-315 (1994).

The term "diabodies" refers to small antibody fragments with two antigen-binding sites, which fragments comprise a heavy-chain variable domain ($V_H$) connected to a light-chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA,* 90:6444-6448 (1993).

An "isolated" antibody is one which has been identified and separated and/or recovered from a component of its natural environment. Contaminant components of its natural environment are materials which would interfere with diagnostic or therapeutic uses for the antibody, and may include enzymes, hormones, and other proteinaceous or nonproteinaceous solutes. In preferred embodiments, the antibody will be purified (1) to greater than 95% by weight of antibody as determined by the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, preferably, silver stain. Isolated antibody includes the antibody in situ within recombinant cells since at least one component of the antibody's natural environment will not be present. Ordinarily, however, isolated antibody will be prepared by at least one purification step.

As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

"Treatment" refers to both therapeutic treatment and prophylactic or preventative measures. Those in need of treatment include those already with the disorder as well as those in which the disorder is to be prevented.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the anti-ErbB2 antibody. This includes chronic and acute disorders or diseases including those pathological conditions which predispose the mammal to the disorder in question. Non-limiting examples of disorders to be treated herein include benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.

The term "therapeutically effective amount" is used to refer to an amount having antiproliferative effect. Preferably, the therapeutically effective amount has apoptotic activity, or is capable of inducing cell death, and preferably death of benign or malignant tumor cells, in particular cancer cells. Efficacy can be measured in conventional ways, depending on the condition to be treated. For cancer therapy, efficacy can, for example, be measured by assessing the time to disease progression (TTP), or determining the response rates (RR) (see the Example below).

The terms "cancer" and "cancerous" refer to or describe the physiological condition in mammals that is typically characterized by unregulated cell growth. Examples of cancer include, but are not limited to, carcinoma, lymphoma, blastoma, sarcoma, and leukemia. More particular examples of such cancers include squamous cell cancer, small-cell lung cancer, non-small cell lung cancer, gastrointestinal cancer, pancreatic cancer, glioblastoma, cervical cancer, ovarian cancer, liver cancer, bladder cancer, hepatoma, breast cancer, colon cancer, colorectal cancer, endometrial carcinoma, salivary gland carcinoma, kidney cancer, liver cancer, prostate cancer, vulval cancer, thyroid cancer, hepatic carcinoma and various types of head and neck cancer.

The term "cytotoxic agent" as used herein refers to a substance that inhibits or prevents the function of cells and/or causes destruction of cells. The term is intended to include radioactive isotopes (e.g. $I^{131}$, $I^{125}$, $Y^{90}$ and $Re^{186}$), chemotherapeutic agents, and toxins such as enzymatically active toxins of bacterial, fungal, plant or animal origin, or fragments thereof.

A "chemotherapeutic agent" is a chemical compound useful in the treatment of cancer. Examples of chemotherapeutic agents include adriamycin, doxorubicin, epirubicin, 5-fluorouracil, cytosine arabinoside ("Ara-C"), cyclophosphamide, thiotepa, busulfan, cytoxin, taxoids, e.g. paclitaxel (TAXOL®, Bristol-Myers Squibb Oncology, Princeton, N.J.) and docetaxel (TAXOTERE®, Rhône-Poulenc Rorer, Antony, France), methotrexate, cisplatin, melphalan, vinblastine, bleomycin, etoposide, ifosfamide, mitomycin C, mitoxantrone, vincristine, vinorelbine, carboplatin, teniposide, daunomycin, carminomycin, aminopterin, dactinomycin, mitomycins, esperamicins (see U.S. Pat. No. 4,675,187), melphalan and other related nitrogen mustards. Also included in this definition are hormonal agents that act to regulate or inhibit hormone action on tumors such as tamoxifen and onapristone.

A "growth inhibitory agent" when used herein refers to a compound or composition which inhibits growth of a cell, especially an ErbB2-overexpressing cancer cell either in vitro or in vivo. Thus, the growth inhibitory agent is one which significantly reduces the percentage of ErbB2 overexpressing cells in S phase. Examples of growth inhibitory agents include agents that block cell cycle progression (at a place other than S phase), such as agents that induce GI arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest GI also spill over into S-phase arrest, for example, DNA alkylating agents such as tamoxifen, prednisone, dacarbazine, mechlorethamine, cisplatin, methotrexate, 5-fluorouracil, and ara-C. Further information can be found in *The Molecular Basis of Cancer*, Mendelsohn and Israel, eds., Chapter 1, entitled "Cell cycle regulation, oncogenes, and antineoplastic drugs" by Murakami et al. (WB Saunders: Philadelphia, 1995), especially p. 13. The 4D5 antibody (and functional equivalents thereof) can also be employed for this purpose.

"Doxorubicin" is an athracycline antibiotic. The full chemical name of doxorubicin is (8S-cis)-10-[(3-amino-2,3,6-trideoxy-α-L-lyxo-hexopyranosyl)oxy]-7,8,9,10-tetrahydro-6,8,11-trihydroxy-8-(hydroxyacetyl)-1-methoxy-5,12-naphthacenedione.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; tumor necrosis factor-α and -β; mullerian-inhibiting substance; mouse gonadotropin-associated peptide; inhibin; activin; vascular endothelial growth factor; integrin; thrombopoietin (TPO); nerve growth factors such as NGF-β; platelet-growth factor; transforming growth factors (TGFs) such as TGF-α and TGF-β; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1a, IL-2, IL-3, IL-4, IL-5, L-6, IL-7, IL-8, IL-9, IL-11, IL-12; a tumor necrosis factor such as TNF-α or TNF-β; and other polypeptide factors including LIF and kit ligand (KL). As used herein, the term cytokine includes proteins from natural sources or from recombinant cell culture and biologically active equivalents of the native sequence cytokines.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" *Biochemical Society Transactions*, 14, pp. 375-382, 615th Meeting Belfast (1986) and Stella et al., "Prodrugs: A Chemical Approach to Targeted Drug Delivery," *Directed Drug Delivery*, Borchardt et al., (ed.), pp. 247-267, Humana Press (1985). The prodrugs of this invention include, but are not limited to, phosphate-containing prodrugs, thiophosphate-containing prodrugs, sulfate-containing prodrugs, peptide-containing prodrugs, D-amino acid-modified prodrugs, glycosylated prodrugs, β-lactamcontaining prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "solid phase" is meant a non-aqueous matrix to which the antibodies used in accordance with the present invention can adhere. Examples of solid phases encompassed herein include those formed partially or entirely of glass (e.g., controlled pore glass), polysaccharides (e.g., agarose), polyacrylamides, polystyrene, polyvinyl alcohol and silicones. In certain embodiments, depending on the context, the solid phase can comprise the well of an assay plate; in others it is a purification column (e.g., an affinity chromatography column). This term also includes a discontinuous solid phase of discrete particles, such as those described in U.S. Pat. No. 4,275,149.

A "liposome" is a small vesicle composed of various types of lipids, phospholipids and/or surfactant which is useful for delivery of a drug (such as the anti-ErbB2 antibodies disclosed herein and, optionally, a chemotherapeutic agent) to a mammal. The components of the liposome are commonly arranged in a bilayer formation, similar to the lipid arrangement of biological membranes.

The term "package insert" is used to refer to instructions customarily included in commercial packages of therapeutic products, that contain information about the indications, usage, dosage, administration, contraindications and/or warnings concerning the use of such therapeutic products.

II. Production of anti-ErbB2 Antibodies

A description follows as to exemplary techniques for the production of the antibodies used in accordance with the present invention. The ErbB2 antigen to be used for production of antibodies may be, e.g., a soluble form of the extracellular domain of ErbB2 or a portion thereof, containing the desired epitope. Alternatively, cells expressing ErbB2 at their cell surface (e.g. NIH-3T3 cells transformed to overexpress ErbB2; or a carcinoma cell line such as SKBR3 cells, see Stancovski et al. *PNAS* (USA) 88:8691-8695 [1991]) can be used to generate antibodies. Other forms of ErbB2 useful for generating antibodies will be apparent to those skilled in the art.

(i) Polyclonal Antibodies

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R_1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ¹/₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(ii) Monoclonal Antibodies

Monoclonal antibodies are obtained from a population of substantially homogeneous antibodies, i.e., the individual antibodies comprising the population are identical except for possible naturally occurring mutations that may be present in minor amounts. Thus, the modifier "monoclonal" indicates the character of the antibody as not being a mixture of discrete antibodies.

For example, the monoclonal antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 [Academic Press, 1986]).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol., 133:3001 (1984); Brodeur et al., Monoclonal Antibody Production Techniques and Applications, pp. 51-63 [Marcel Dekker, Inc., New York, 1987]).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice, pp. 59-103 [Academic Press, 1986]). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). The hybridoma cells serve as a preferred source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin protein, to obtain the synthesis of monoclonal antibodies in the recombinant host cells. Review articles on recombinant expression in bacteria of DNA encoding the antibody include Skerra et al., Curr. Opinion in Immunol., 5:256-262 (1993) and Pluckthun, Immunol. Revs., 130: 151-188 (1992).

In a further embodiment, antibodies or antibody fragments can be isolated from antibody phage libraries generated using the techniques described in McCafferty et al., Nature, 348: 552-554(1990). Clackson et al., Nature, 352:624-628(1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 [1992]), as well as combinatorial infection and in vivo recombination as a strategy for constructing very large phage libraries (Waterhouse et al., Nuc. Acids. Res., 21:2265-2266 [1993]). Thus, these techniques are viable alternatives to traditional monoclonal antibody hybridoma techniques for isolation of monoclonal antibodies.

The DNA also may be modified, for example, by substituting the coding sequence for human heavy- and light-chain constant domains in place of the homologous murine sequences (U.S. Pat. No. 4,816,567; Morrison, et al., Proc.

Natl Acad. Sci. USA, 81:6851 [1984]), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

(iii) Humanized and Human Antibodies

Methods for humanizing non-human antibodies are well known in the art. Preferably, a humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525(1986); Riechmann et al., Nature, 332:323-327 (1988); Verhoeyen et al., Science, 239:1534-1536 [1988]), by substituting rodent CDRs or CDR sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "bestfit" method, the sequence of the variable domain of a rodent antibody is screened against the entire library of known human variable-domain sequences. The human sequence which is closest to that of the rodent is then accepted as the human framework region (FR) for the humanized antibody (Sims et al., J. Immunol., 151:2296 (1993); Chothia et al., J. Mol. Biol., 196:901 [1987]). Another method uses a particular framework region derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immnol., 151:2623 [1993]).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno., 7:33 (1993). Human antibodies can also be derived from phage-display libraries (Hoogenboom et al., J. Mol. Biol., 227:381 (1991); Marks et al., J. Mol. Biol., 222:581-597 [1991]).

(iv) Antibody Fragments

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 [1985]). However, these fragments can now be produced directly by recombinant host cells. For example, the antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 [1992]). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

(v) Bispecific Antibodies

Bispecific antibodies are antibodies that have binding specificities for at least two different epitopes. Exemplary bispecific antibodies may bind to two different epitopes of the ErbB2 protein. For example, one arm may bind an epitope in Domain 1 of ErbB2 such as the 7C2/7F3 epitope, the other may bind a different ErbB2 epitope, e.g. the 4D5 epitope. Other such antibodies may combine an ErbB2 binding site with binding site(s) for EGFR, ErbB3 and/or ErbB4. Alternatively, an anti-ErbB2 arm may be combined with an arm which binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the ErbB2-expressing cell. Bispecific antibodies may also be used to localize cytotoxic agents to cells which express ErbB2. These antibodies possess an ErbB2-binding arm and an arm which binds the cytotoxic agent (e.g. saporin, anti-interferon-α, vinca alkaloid, ricin A chain, methotrexate or radioactive isotope hapten). Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 [1983]). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229:81 (1985) describe a procedure wherein intact antibodies are proteolytically cleaved to generate $F(ab')_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175:217-225 (1992) describe the production of a fully humanized bispecific antibody $F(ab')_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. *Natl. Acad. Sci.* USA, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994).

Antibodies with more than two valencies are contemplated. For example, trispecific antibodies can be prepared. Tutt et al. *J. Immunol.* 147:60 (1991).

(vi) Screening for Antibodies with the Desired Properties

Techniques for generating antibodies have been described above. Those antibodies having the characteristics described herein are selected.

To select for antibodies which induce cell death, loss of membrane integrity as indicated by, e.g., PI, trypan blue or 7AAD uptake is assessed relative to control. The preferred assay is the "PI uptake assay using BT474 cells". According to this assay, BT474 cells (which can be obtained from the American Type Culture Collection [Rockville, Md.]) are cultured in Dulbecco's Modified Eagle Medium (D-MEM): Ham's F-12 (50:50) supplemented with 10% heat-inactivated FBS (Hyclone) and 2 mM L-glutamine. (Thus, the assay is performed in the absence of complement and immune effector cells). The BT474 cells are seeded at a density of $3 \times 10^6$ per dish in $100 \times 20$ mm dishes and allowed to attach overnight. The medium is then removed and replaced with fresh medium alone or medium containing 10 µg/ml of the appropriate MAb. The cells are incubated for a 3 day time period. Following each treatment, monolayers are washed with PBS and detached by trypsinization. Cells are then centrifuged at 1200 rpm for 5 minutes at 4° C., the pellet resuspended in 3 ml ice cold $Ca^{2+}$ binding buffer (10 mM Hepes, pH 7.4, 140 mM NaCl, 2.5 mM $CaCl_2$) and aliquoted into 35 mm strainer-capped 12×75 tubes (1 ml per tube, 3 tubes per treatment group) for removal of cell clumps. Tubes then receive PI (10 µg/ml). Samples may be analyzed using a FACSCAN™ flow cytometer and FACSCONVERT™ CellQuest software (Becton Dickinson). Those antibodies which induce statistically significant levels of cell death as determined by PI uptake are selected.

In order to select for antibodies which induce apoptosis, an "annexin binding assay using BT474 cells" is available. The BT474 cells are cultured and seeded in dishes as discussed in the preceding paragraph. The medium is then removed and replaced with fresh medium alone or medium containing 10 µg/ml of the MAb. Following a three day incubation period, monolayers are washed with PBS and detached by trypsinization. Cells are then centrifuged, resuspended in $Ca^{2+}$ binding buffer and aliquoted into tubes as discussed above for the cell death assay. Tubes then receive labeled annexin (e.g. annexin V-FTIC) (1 µg/ml). Samples may be analyzed using a FAC-SCAN™ flow cytometer and FACSCONVERT™ CellQuest software (Becton Dickinson). Those antibodies which induce statistically significant levels of annexin binding relative to control are selected as apoptosis-inducing antibodies.

In addition to the annexin binding assay, a "DNA staining assay using BT474 cells" is available. In order to perform this assay, BT474 cells which have been treated with the antibody of interest as described in the preceding two paragraphs are incubated with 9 µg/ml HOECHST 33342™ for 2 hr at 37° C., then analyzed on an EPICS ELITE™ flow cytometer (Coulter Corporation) using MODFIT LT™ software (Verity Software House). Antibodies which induce a change in the percentage of apoptotic cells which is 2 fold or greater (and preferably 3 fold or greater) than untreated cells (up to 100% apoptotic cells) may be selected as pro-apoptotic antibodies using this assay.

To screen for antibodies which bind to an epitope on ErbB2 bound by an antibody of interest, a routine cross-blocking assay such as that described in *Antibodies, A Laboratory Manual*, Cold Spring Harbor Laboratory, Ed Harlow and David Lane (1988), can be performed. Alternatively, epitope mapping can be performed by methods known in the art.

To identify anti-ErbB2 antibodies which inhibit growth of SKBR3 cells in cell culture by 50-100%, the SKBR3 assay described in WO89/06692 can be performed. According to this assay, SKBR3 cells are grown in a 1:1 mixture of F12 and DMEM medium supplemented with 10% fetal bovine serum, glutamine and penicillinstreptomycin. The SKBR3 cells are plated at 20,000 cells in a 35 mm cell culture dish (2 mls/35 mm dish). 2.5 µg/ml of the anti-ErbB2 antibody is added per dish. After six days, the number of cells, compared to untreated cells are counted using an electronic COULTER™ cell counter. Those antibodies which inhibit growth of the SKBR3 cells by 50-100% are selected for combination with the apoptotic antibodies as desired.

(vii) Effector Function Engineering

It may be desirable to modify the antibody of the invention with respect to effector function, so as to enhance the effectiveness of the antibody in treating cancer, for example. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp. Med.* 176:1191-1195 (1992) and Shopes, B. *J. Immunol.* 148:2918-2922 (1992). Homodimeric antibodies with enhanced anti-tumor activity may also be prepared using heterobifunctional cross-linkers as described in Wolff et al. *Cancer Research* 53:2560-2565 (1993). Alternatively, an antibody can be engineered which has dual Fc regions and may thereby have enhanced complement lysis and ADCC capabilities. See Stevenson et al. *Anti-Cancer Drug Design* 3:219-230 (1989).

(viii) Immunoconjugates

The invention also pertains to immunoconjugates comprising the antibody described herein conjugated to a cytotoxic agent such as a chemotherapeutic agent, toxin (e.g. an enzymatically active toxin of bacterial, fungal, plant or animal origin, or fragments thereof), or a radioactive isotope (i.e., a radioconjugate).

Chemotherapeutic agents useful in the generation of such immunoconjugates have been described above. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugated anti-ErbB2 antibodies. Examples include $^{212}Bi$, $^{131}I$, $^{131}In$, $^{90}Y$ and $^{186}Re$.

Conjugates of the antibody and cytotoxic agent are made using a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaredehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. *Science* 238:1098 (1987). Carbon-14-labeled 1-isothiocyanatobenzyl-3-methyldiethylene triaminepentaacetic acid (MXDTPA) is an exemplary chelating agent for conjugation of radionucleotide to the antibody. See WO94/11026.

In another embodiment, the antibody may be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g. avidin) which is conjugated to a cytotoxic agent (e.g. a radionucleotide).

(ix) Immunoliposomes

The anti-ErbB2 antibodies disclosed herein may also be formulated as immunoliposomes. Liposomes containing the antibody are prepared by methods known in the art, such as described in Epstein et al., *Proc. Natl. Acad. Sci.* USA, 82:3688 (1985); Hwang et al., *Proc. Natl. Acad. Sci.* USA, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al. *Biol. Chem.* 257: 286-288 (1982) via a disulfide interchange reaction. A chemotherapeutic agent is optionally contained within the liposome. See Gabizon et al. *J. National Cancer Inst.* 81(19)1484 (1989).

(x) Antibody Dependent Enzyme Mediated Prodrug Therapy (ADEPT)

The antibodies of the present invention may also be used in ADEPT by conjugating the antibody to a prodrug-activating enzyme which converts a prodrug (e.g. a peptidyl chemotherapeutic agent, see WO81/01145) to an active anti-cancer drug. See, for example, WO. 88/07378 and U.S. Pat. No. 4,975,278.

The enzyme component of the immunoconjugate useful for ADEPT includes any enzyme capable of acting on a prodrug in such a way so as to covert it into its more active, cytotoxic form.

Enzymes that are useful in the method of this invention include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as serratia protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs of the invention into free active drugs (see, e.g., Massey, *Nature* 328:457-458 [1987]). Antibody-abzyme conjugates can be prepared as described herein for delivery of the abzyme to a tumor cell population.

The enzymes of this invention can be covalently bound to the anti-ErbB2 antibodies by techniques well known in the art such as the use of the heterobifunctional crosslinking reagents discussed above. Alternatively, fusion proteins comprising at least the antigen binding region of an antibody of the invention linked to at least a functionally active portion of an enzyme of the invention can be constructed using recombinant DNA techniques well known in the art (see, e.g., Neuberger et al., *Nature*, 312:604-608 [1984]).

(xi) Antibody-salvage Receptor Binding Epitope Fusions

In certain embodiments of the invention, it may be desirable to use an antibody fragment, rather than an intact antibody, to increase tumor penetration, for example. In this case, it may be desirable to modify the antibody fragment in order to increase its serum half life. This may be achieved, for example, by incorporation of a salvage receptor binding epitope into the antibody fragment (e.g. by mutation of the appropriate region in the antibody fragment or by incorporating the epitope into a peptide tag that is then fused to the antibody fragment at either end or in the middle, e.g., by DNA or peptide synthesis).

A systematic method for preparing such an antibody variant having an increased in vivo half-life comprises several steps. The first involves identifying the sequence and conformation of a salvage receptor binding epitope of an Fc region of an IgG molecule. Once this epitope is identified, the sequence of the antibody of interest is modified to include the sequence and conformation of the identified binding epitope. After the sequence is mutated, the antibody variant is tested to see if it has a longer in vivo half-life than that of the original antibody. If the antibody variant does not have a longer in vivo half-life upon testing, its sequence is further altered to include the sequence and conformation of the identified binding epitope. The altered antibody is tested for longer in vivo half-life, and this process is continued until a molecule is obtained that exhibits a longer in vivo half-life.

The salvage receptor binding epitope being thus incorporated into the antibody of interest is any suitable such epitope as defined above, and its nature will depend, e.g., on the type of antibody being modified. The transfer is made such that the antibody of interest still possesses the biological activities described herein.

The epitope preferably constitutes a region wherein any one or more amino acid residues from one or two loops of a Fc domain are transferred to an analogous position of the antibody fragment. Even more preferably, three or more residues from one or two loops of the Fc domain are transferred. Still more preferred, the epitope is taken from the CH2 domain of the Fc region (e.g., of an IgG) and transferred to the CH1, CH3, or $V_H$ region, or more than one such region, of the antibody. Alternatively, the epitope is taken from the CH2 domain of the Fc region and transferred to the $C_L$ region or $V_L$ region, or both, of the antibody fragment.

In one most preferred embodiment, the salvage receptor binding epitope comprises the sequence (5' to 3'): PKNSSMISNTP (SEQ ID NO:3), and optionally further comprises a sequence selected from the group consisting of HQSLGTQ (SEQ ID NO:4), HQNLSDGK (SEQ ID NO:5), HQNISDGK (SEQ ID NO:6), or VISSHLGQ (SEQ ID NO:7), particularly where the antibody fragment is a Fab or F(ab')₂. In another most preferred embodiment, the salvage receptor binding epitope is a polypeptide containing the sequence(s)(5' to 3'): HQNLSDGK (SEQ ID NO:5), HQNISDGK (SEQ ID NO:6), or VISSHLGQ (SEQ ID NO:7) and the sequence: PKNSSMISNTP (SEQ ID NO:3).

(xii) Purification of Anti-ErbB2 Antibody

When using recombinant techniques, the antibody can be produced intracellularly, in the periplasmic space, or directly secreted into the medium. If the antibody is produced intracellularly, as a first step, the particulate debris, either host cells or lysed fragments, is removed, for example, by centrifugation or ultrafiltration. Carter et al., *Bio/Technology* 10:163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are preferably first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being the preferred purification technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., *J. Immnol. Meth.* 62:1-13 [1983]). Protein G is recommended for all mouse isotypes and for human γ3 (Guss et al., *EMBO J.* 5:15671575 [1986]). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, preferably performed at low salt concentrations (e.g. from about 0-0.25M salt).

III. Pharmaceutical Formulations

Therapeutic formulations of the antibodies used in accordance with the present invention are prepared for storage by mixing an antibody having the desired degree of purity with optional pharmaceutically acceptable carriers, excipients or stabilizers (*Remington's Pharmaceutical Sciences* 16th edition, Osol, A. Ed. [1980]), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

The formulation herein may also contain more than one active compound as necessary for the particular indication being treated, preferably those with complementary activities that do not adversely affect each other. For example, it may be desirable to further provide antibodies which bind to EGFR, ErbB2 (e.g. an antibody which binds a different epitope on ErbB2), ErbB3, ErbB4, or vascular endothelial factor (VEGF) in the one formulation. Alternatively, or in addition, the composition may comprise a cytotoxic agent, cytokine or growth inhibitory agent, provided that the cytotoxic agent is other than an anthracycline derivative, e.g. doxorubicin, or epirubicin. Such molecules are suitably present in combination in amounts that are effective for the purpose intended.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nanoparticles and nanocapsules) or in macroemulsions. Such techniques are disclosed in *Remington's Pharmaceutical Sciences* 16th edition, Osol, A. Ed. (1980).

The formulations to be used for in vivo administration must be sterile. This is readily accomplished by filtration through sterile filtration membranes.

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they may denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization may be achieved by modifying sulfhydryl residues, lyophilizing from acidic solutions, controlling moisture content, using appropriate additives, and developing specific polymer matrix compositions.

IV. Treatment with the Anti-ErbB2 Antibodies

It is contemplated that, according to the present invention, the anti-ErbB2 antibodies may be used to treat various conditions characterized by overexpression and/or activation of the ErbB2 receptor. Exemplary conditions or disorders include benign or malignant tumors (e.g. renal, liver, kidney, bladder, breast, gastric, ovarian, colorectal, prostate, pancreatic, lung, vulval, thyroid, hepatic carcinomas; sarcomas; glioblastomas; and various head and neck tumors); leukemias and lymphoid malignancies; other disorders such as neuronal, glial, astrocytal, hypothalamic and other glandular, macrophagal, epithelial, stromal and blastocoelic disorders; and inflammatory, angiogenic and immunologic disorders.

The antibodies of the invention are administered to a human patient, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Intravenous administration of the antibody is preferred.

The treatment of the present invention involved the combined administration of an anti-ErbB2 antibody and a chemotherapeutic agent, other than an anthracycline derivative. The combined administration includes coadministration, using separate formulations or a single pharmaceutical formulation, and consecutive administration in either order, wherein preferably there is a time period while both (or all) active agents simultaneously exert their biological activities. Preparation and dosing schedules for such chemotherapeutic agents may be used according to manufacturers' instructions or as determined empirically by the skilled practitioner. Preparation and dosing schedules for such chemotherapy are also described in Chemotherapy Service Ed., M. C. Perry, Williams & Wilkins, Baltimore, Md. (1992). The chemotherapeutic agent may precede, or follow administration of the antibody or may be given simultaneously therewith. The antibody may be combined with an anti-estrogen compound such as tamoxifen or an anti-progesterone such as onapristone (see, EP 616 812) in dosages known for such molecules.

It may be desirable to also administer antibodies against other tumor associated antigens, such as antibodies which bind to the EGFR, ErbB3, ErbB4, or vascular endothelial factor (VEGF). Alternatively, or in addition, two or more anti-ErbB2 antibodies may be co-administered to the patient. Sometimes, it may be beneficial to also administer one or more cytokines to the patient. In a preferred embodiment, the ErbB2 antibody is co-administered with a growth inhibitory agent. For example, the growth inhibitory agent may be administered first, followed by the ErbB2 antibody. However, simultaneous administration or administration of the ErbB2 antibody first is also contemplated. Suitable dosages for the growth inhibitory agent are those presently used and may be lowered due to the combined action (synergy) of the growth inhibitory agent and anti-ErbB2 antibody.

For the prevention or treatment of disease, the appropriate dosage of antibody will depend on the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

Depending on the type and severity of the disease, about 1 μg/kg to 15 mg/kg (e.g. 0.1-20 mg/kg) of antibody is an initial candidate dosage for administration to the patient, whether, for example, by one or more separate administrations, or by continuous infusion. A typical daily dosage might range from about 1 μg/kg to 100 mg/kg or more, depending on the factors mentioned above. For repeated administrations over several days or longer, depending on the condition, the treatment is sustained until a desired suppression of disease symptoms occurs. However, other dosage regimens may be useful. The progress of this therapy is easily monitored by conventional techniques and assays.

Further information about suitable dosages is provided in the Example below.

V. Articles of Manufacture

In another embodiment of the invention, an article of manufacture containing materials useful for the treatment of the disorders described above is provided. The article of manufacture comprises a container, a label and a package insert. Suitable containers include, for example, bottles, vials, syringes, etc. The containers may be formed from a variety of materials such as glass or plastic. The container holds a composition which is effective for treating the condition and may have a sterile access port (for example the container may be an intravenous solution bag or a vial having a stopper pierceable by a hypodermic injection needle). At least one active agent in the composition is an anti-ErbB2 antibody. The label on, or associated with, the container indicates that the composition is used for treating the condition of choice. The article of manufacture may further comprise a second container comprising a pharmaceutically-acceptable buffer, such as phosphate-buffered saline, Ringer's solution and dextrose solution. It may further include other materials desirable from a commercial and user standpoint, including other buffers, diluents, filters, needles, and syringes. In addition, the article of manufacture comprises a package inserts with instructions for use, including a warning that the composition is not to be used in combination with anthacycline-type chemotherapeutic agent, e.g. doxorubicin, or epirubicin.

DEPOSIT OF MATERIALS

The following hybridoma cell lines have been deposited with the American Type Culture Collection, 12301 Parklawn Drive, Rockville, Md., USA (ATCC):

| Antibody Designation | ATCC No. | Deposit Date |
|---|---|---|
| 7C2 | ATCC HB-12215 | Oct. 17, 1996 |
| 7F3 | ATCC HB-12216 | Oct. 17, 1996 |
| 4D5 | ATCC CRL 10463 | May 24, 1990 |

Further details of the invention are illustrated by the following non-limiting Example.

EXAMPLE

Materials and Methods

Anti-ErbB2 monoclonal antibody The anti-ErbB2 IgG$_1$K murine monoclonal antibody 4D5, specific for the extracellular domain of ErbB2, was produced as described in Fendly et al., *Cancer Research* 5o:1550-1558 (1990) and WO89/06692. Briefly, NIH 3T3HER2-3$_{400}$ cells (expressing approximately 1×10$^5$ ErbB2 molecules/cell) produced as described in Hudziak et al. *Proc. Natl. Acad. Sci.* (USA) 84:7159 (1987) were harvested with phosphate buffered saline (PBS) containing 25 mM EDTA and used to immunize BALB/c mice. The mice were given injections i.p. of 10$^7$ cells in 0.5 ml PBS on weeks, 0, 2, 5 and 7. The mice with antisera that immunoprecipitated $^{32}$P-labeled ErbB2 were given i.p. injections of a wheat germ agglutinin-Sepharose (WGA) purified ErbB2 membrane extract on weeks 9 and 13. This was followed by an i.v. injection of 0.1 ml of the ErbB2 preparation and the splenocytes were fused with mouse myeloma line X63-Ag8.653. Hybridoma supernatants were screened for ErbB2-binding by ELISA and radioimmunoprecipitation. MOPC-21 (IgG1), (Cappell, Durham, N.C.), was used as an isotype-matched control.

The treatment was performed with a humanized version of the murine 4D5 antibody (HERCEPTIN®). The humanized antibody was engineered by inserting the complementarity determining regions of the murine 4D5 antibody into the framework of a consensus human immunoglobulin IgG$_1$ (IgG$_1$) (Carter et al., *Proc. Natl. Acad. Sci.* USA 89:4285-4289 [1992]). The resulting humanized anti-ErbB2 monoclonal antibody has high affinity for p185$^{HER2}$ (Dillohiation constant [K$_d$]=0.1 nmol/L), markedly inhibits, in vitro and in human xenografts, the growth of breast cancer cells that contain high levels of $p185^{HER2}$, induces antibody-dependent cellular cytotoxicity (ADCC), and has been found clinically active, as a single agent, in patients with ErbB2-overexpressing metastatic breast cancers that had received extensive prior therapy. HERCEPTIN® is produced by a genetically engineered Chinese Hamster Ovary (CHO) cell line, grown in large scale, that secretes the antibody into the culture medium. The antibody is purified from the CHO culture media using standard chromatographic and filtration methods. Each lot of antibody used in this study was assayed to verify identity, purity, and potency, as well as to meet Food and Drug Administration requirements for sterility and safety.

Eligibility Criteria Patients had to fulfill all of the following criteria to be eligible for study admission:

Metastatic breast cancer

Overexpression of the ErbB2 (HER2) oncogene (2+ to 3+ as determined by immunohistochemistry or fluorescence in situ hybridization (FISH). [Tumor expression of ErbB2 can be determined by immunohistochemical analysis, as previously described (Slamon et al., [1987] and [1989], supra), of a set of thin sections prepared from the patient's paraffin-archived tumor blocks. The primary detecting antibody used is murine 4D5 MAb, which has the same CDRs as the humanized antibody used for the treatment. Tumors are considered to overexpress ErbB2 if at least 25% of tumor cells exhibit characteristic membrane staining for $p185^{HER2}$].

Bidimensionally measurable disease (including lytic bone lesions) by radiographic means, physical examination, or photographs Measurable disease was defined as any mass reproducibly measurable in two perpendicular diameters by physical examination, X-ray (plain films), computerized tomography (CT), magnetic resonance imaging (MRI), ultrasound, or photographs.

Osteoblastic metastases, pleural effusions, or ascites were not considered to be measurable. Measurable lesions must be at least 1 cm in greatest dimension. Enumeration of evaluable sites of metastatic disease and number of lesions in an evaluable site (e.g. lung) had to be recorded on the appropriate Case Report Form (CRF). If a large number of pulmonary or hepatic lesions were present, the six largest lesions per site were followed.

The ability to understand and willingness to sign a written informed consent form Women≧18 years Suitable candidates for receiving concomitant cytotoxic chemotherapy as evidenced by screening laboratory assessments of hematologic, renal, hepatic, and metabolic functions.

Exclusion Criteria Patients with any of the following were excluded from study entry:

Prior cytotoxic chemotherapy for metastatic breast cancer

Patients may have received prior hormonal therapy (e.g. tamoxifen) for metastatic disease or cytotoxic therapy in the adjuvant setting.

Concomitant malignancy that has not been curatively treated

A performance status of <60% on the Karnofsky scale

Pregnant or nursing women; women of childbearing potential, unless using effective contraception as determined by the investigator Bilateral breast cancer (either both primary tumors must have 2+ to 3+HER2 overexpression, or the metastatic site must have 2+ to 3+HER2 overexpression)

Use of investigational or unlicensed agents within 30 days prior to study entry

Clinically unstable or untreated metastases to the brain (e.g. requiring radiation therapy)

Based upon the foregoing criteria, 469 patients were chosen, and enrolled in the study. Half the patients (stratified by chemotherapy) were randomized to additionally receive the HERCEPTIN® antibody (see below).

Administration and Dosage

Anti-ErbB2 Antibody

On day 0, a 4 mg/kg dose of humanized anti-ErbB2 antibody (HERCEPTIN®, H) was administered intravenously, over a 90-minute period. Beginning on day 7, patients received weekly administration of 2 mg/kg antibody (i.v.) over a 90-minute period.

Chemotherapy

The patients received one of two chemotherapy regiments for a minimum of six cycles, provided their disease was not progressing: a) cyclophosphamide and doxorubicin or epirubicin (AC), if patients have not received anthracycline therapy in the adjuvant setting, or b) paclitaxel (T, TAXOL®), if patients have received any anthracycline therapy in the adjuvant setting. The initial dose of the HERCEPTIN® antibody preceded the first cycle of either chemotherapy regimen by 24 hours. Subsequent doses of the antibody were given immediately before chemotherapy administration, if the initial dose of the antibody was well tolerated. If the first dose of the antibody was not well tolerated, subsequent infusions continued to precede chemotherapy administration by 24 hours. Patients were permitted to continue receiving chemotherapy beyond six cycles if, in the opinion of the treating physician, they were continuing to receive treatment benefit.

Cyclophosphamide (600 mg/m$^2$) was given either by iv push over a minimum period of 3 minutes or by infusion over a maximum period of 2 hours.

Doxorubicin (60 mg/m$^2$) or epirubicin (75 mg/m$^2$) were given either by slow iv push over a minimum period of 3-5 minutes or by infusion over a maximum period of 2 hours, according to institutional protocol.

Paclitaxel (TAXOL®) was given at a dose of 175 mg/m$^2$ over 3 hours by intravenous administration. All patients receiving paclitaxel were premedicated with dexamethasone (or its equivalent) 20 mg×2, administered orally 12 and 6 hours prior to paclitaxel; diphenhydramine (or its equivalent) 50 mg, iv, administered 30 minutes prior to paclitaxel, and dimetidine (or another H2 blocker) 300 mg, iv, administered 30 minutes prior to paclitaxel.

Response Criteria

Progressive Disease Objective evidence of an increase of 25% or more in any measurable lesion. Progressive disease also includes those instances when new lesions have appeared. For bone lesions, progression is defined as a 25% increase in objective measurement by plain film, CT, MRI; symptomatic new lesions not due to fracture; or requirement for palliative radiotherapy.

Complete Response Disappearance of all radiographically and/or visually apparent tumor for a minimum of 4 weeks. Skin and chest wall complete responses had to be confirmed by biopsy.

Partial Response A reduction of at least 50% in the sum of the products of the perpendicular diameters of all measurable lesions for a minimum period of 4 weeks. No new lesions may have appeared, nor may any lesions have progressed in size.

Minor Response A reduction of 25% to 49% in the sum of the products of the perpendicular diameters of all measurable lesions. No new lesions may have appeared, nor may any lesions have progressed in size.

Stable Disease No change of greater than 25% in the size of measurable lesions. No lesions may have appeared.

Time to disease progression (TTP) was calculated from the beginning of therapy to progression. Confidence limits for response rates were calculated using the exact method for a single proportion. (Fleiss, J L, *Statistical Methods for Rates and Proportions* (ed.2), New York, N.Y., Wiley, 1981, pp 13-17).

RESULTS

At a median follow-up of 10.5 months, assessments of time to disease progression (TTP in months) and response rates (RR) showed a significant augmentation of the chemotherapeutic effect by HERCEPTIN®, without increase in overall severe adverse events (AE):

|  | Enrolled | TTP(months) | RR(%) | AE(%) |
|---|---|---|---|---|
| CRx | 234 | 5.5 | 36.2 | 66 |
| CRx + H | 235 | 8.6* | 62.00** | 69 |
| AC | 145 | 6.5 | 42.1 | 71 |
| AC + H | 146 | 9.0 | 64.9 | 68 |
| T | 89 | 4.2 | 25.0 | 59 |
| T + H | 89 | 7.1 | 57.3 | 70 |

*$p < 0.001$ by log-rank test
**$p < 0.001$ by $X^2$ test
CRx: chemotherapy
AC: anthracycline/cyclophosphamide treatment
H: HERCEPTIN®
T: TAXOL®

A syndrome of myocardial dysfunction similar to that observed with anthracyclines was reported more commonly with a combined treatment of AC+H (18% Grade ¾) than with AC alone (3%), T (0%), or T+H (2%).

These data indicate that the combination of anti-ErbB2 antibody treatment with chemotherapy markedly increases the clinical benefit, as assessed by response rates and the evaluation of disease progression. However, due to the increased cardiac side-effects of doxorubicin or epirubicin, the combined use of anthracyclines with anti-ErbB2 antibody therapy is contraindicated. The results, taking into account risk and benefit, favor the combined treatment with HERCEPTIN® and paclitaxel (TAXOL®).

The disclosures of all citations in the specification are expressly incorporated herein by reference.

The invention claimed is:

1. A method for the treatment of a human patient with breast cancer that overexpresses ErbB2 receptor, comprising administering a combination of an antibody that binds ErbB2, a taxoid, and a further growth inhibitory agent to the human patient in an amount effective to extend the time to disease progression in the human patient, wherein the antibody binds to epitope 4D5 within the ErbB2 extracellular domain sequence.

2. The method of claim 1 wherein the antibody is a humanized 4D5 anti-ErbB2 antibody.

3. The method of claim 1 wherein the antibody crossblocks binding of 4D5 to the ErbB2 extracellular domain sequence.

4. The method of claim 1 wherein the antibody binds to amino acid residues in the region from about residue 529 to about residue 625 of the ErbB2 extracellular domain sequence.

5. A method for the treatment of a human patient with breast cancer characterized by overexpression of ErbB2 receptor, comprising administering an effective amount of a combination of an anti-ErbB2 antibody which binds epitope 4D5 within the ErbB2 extracellular domain sequence, a taxoid, and a further therapeutic agent, to the human patient.

6. The method of claim 5 wherein the breast cancer is metastatic breast carcinoma.

7. The method of claim 5 wherein the antibody is a humanized 4D5 anti-ErbB2 antibody.

8. The method of claim 7 wherein the antibody is administered as a 4 mg/kg dose and then weekly administration of 2 mg/kg.

9. The method of claim 5 wherein the taxoid is paclitaxel.

10. The method of claim 5 wherein efficacy is measured by determining the time to disease progression or the response rate.

11. The method of claim 5, wherein the further therapeutic agent is selected from the group consisting of: another ErbB2 antibody, EGFR antibody, ErbB3 antibody, ErbB4 antibody, vascular endothelial growth factor (VEGF) antibody, cytokine, and growth inhibitory agent.

12. The method of claim 5 wherein the further therapeutic agent is another ErbB2 antibody.

13. The method of claim 5 wherein the further therapeutic agent is a vascular endothelial growth factor (VEGF) antibody.

14. The method of claim 5 wherein the further therapeutic agent is a growth inhibitory agent.

15. The method of claim 14 wherein the growth inhibitory agent is a DNA alkylating agent.

16. A method for the treatment of a human patient with ErbB2 overexpressing breast cancer, comprising administering a combination of an antibody that binds epitope 4D5 within the ErbB2 extracellular domain sequence, a taxoid and a further growth inhibitory agent, in the absence of an anthracycline derivative, to the human patient in an amount effective to extend the time to disease progression in the human patient.

17. The method of claim 16 wherein the breast cancer is metastatic breast carcinoma.

* * * * *

(12) INTER PARTES REVIEW CERTIFICATE (1891st)
United States Patent
Paton et al.

(10) Number: US 7,892,549 K1
(45) Certificate Issued: Feb. 9, 2021

(54) TREATMENT WITH ANTI-ERBB2 ANTIBODIES

(75) Inventors: Virginia E. Paton; Steven Shak; Susan D. Hellmann

(73) Assignee: Genentech, Inc.

Trial Numbers:

IPR2017-00737 filed Jan. 20, 2017
IPR2017-01960 filed Aug. 25, 2017
IPR2017-01122 filed Mar. 21, 2017

Inter Partes Review Certificate for:

Patent No.: 7,892,549
Issued: Feb. 22, 2011
Appl. No.: 10/356,824
Filed: Feb. 3, 2003

The results of IPR2017-00737 joined with IPR2017-01960; IPR2017-01122 are reflected in this inter partes review certificate under 35 U.S.C. 318(b).

INTER PARTES REVIEW CERTIFICATE
U.S. Patent 7,892,549 K1
Trial No. IPR2017-00737
Certificate Issued Feb. 9, 2021

AS A RESULT OF THE INTER PARTES REVIEW PROCEEDING, IT HAS BEEN DETERMINED THAT:

Claims 1-17 are cancelled.

\* \* \* \* \*